(12) United States Patent
Liu et al.

(10) Patent No.: US 11,771,885 B2
(45) Date of Patent: Oct. 3, 2023

(54) SYSTEMS AND METHODS FOR PREDICTING PATIENT HEALTH STATUS

(71) Applicant: ABIOMED, Inc., Danvers, MA (US)

(72) Inventors: Chen Liu, Danvers, MA (US); Ahmad El Katerji, Danvers, MA (US); Scott Corbett, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 0 days.

(21) Appl. No.: 17/724,137

(22) Filed: Apr. 19, 2022

(65) Prior Publication Data

US 2022/0241579 A1 Aug. 4, 2022

Related U.S. Application Data

(62) Division of application No. 16/230,575, filed on Dec. 21, 2018, now Pat. No. 11,338,125.

(Continued)

(51) Int. Cl.
*A61M 60/50* (2021.01)
*G16H 50/20* (2018.01)
(Continued)

(52) U.S. Cl.
CPC ............ *A61M 60/50* (2021.01); *A61B 5/00* (2013.01); *A61M 60/135* (2021.01);
(Continued)

(58) Field of Classification Search
CPC .. A61M 2205/3303; A61M 2205/3365; A61M 2205/50; A61M 2205/502; A61M 2205/52; A61M 2205/584; A61M 2230/06; A61M 2230/20; A61M 2230/208; A61M 2230/30; A61M 2230/43
See application file for complete search history.

(56) References Cited

U.S. PATENT DOCUMENTS

2017/0232167 A1 8/2017 Spanier et al.

FOREIGN PATENT DOCUMENTS

JP 2000512191 A 9/2000
JP 2013524865 A 6/2013
(Continued)

OTHER PUBLICATIONS

Office Action issued in corresponding Indian Patent Application No. 202017029455 dated Apr. 27, 2022, (6 pp.).
(Continued)

*Primary Examiner* — Mallika D Fairchild
(74) *Attorney, Agent, or Firm* — BOTOS CHURCHILL IP LAW LLP

(57) ABSTRACT

Systems and methods are provided herein for treating a patient in cardiogenic shock. An intravascular heart pump system is inserted into vasculature of the patient. The heart pump system has a cannula, pump outlet, pump inlet, and rotor. The heart pump system is positioned within the patient such that the cannula extends across the patient's aortic valve, the pump inlet is located within the patient's left ventricle, and the pump outlet is located within the patient's aorta. Data related to time-varying parameters of the heart pump system is acquired from the heart pump system. A plurality of features are extracted from the data. A probability of survival of the patient is determined based on the plurality of features and using a prediction model. The heart pump system is operated to treat the patient.

20 Claims, 15 Drawing Sheets

Related U.S. Application Data

(60) Provisional application No. 62/609,158, filed on Dec. 21, 2017.

(51) Int. Cl.

| | | |
|---|---|---|
| *A61B 5/00* | (2006.01) | |
| *G16H 50/00* | (2018.01) | |
| *G16H 20/17* | (2018.01) | |
| *G16H 20/40* | (2018.01) | |
| *A61M 60/422* | (2021.01) | |
| *A61M 60/139* | (2021.01) | |
| *A61M 60/216* | (2021.01) | |
| *A61M 60/857* | (2021.01) | |
| *A61M 60/816* | (2021.01) | |
| *A61M 60/531* | (2021.01) | |
| *A61M 60/585* | (2021.01) | |
| *A61M 60/538* | (2021.01) | |
| *A61M 60/178* | (2021.01) | |
| *A61M 60/135* | (2021.01) | |
| *G06N 5/045* | (2023.01) | |
| *G06N 20/00* | (2019.01) | |
| *A61M 60/148* | (2021.01) | |
| *A61M 60/205* | (2021.01) | |

(52) U.S. Cl.
CPC ........ *A61M 60/139* (2021.01); *A61M 60/178* (2021.01); *A61M 60/216* (2021.01); *A61M 60/422* (2021.01); *A61M 60/531* (2021.01); *A61M 60/538* (2021.01); *A61M 60/585* (2021.01); *A61M 60/816* (2021.01); *A61M 60/857* (2021.01); *G16H 20/17* (2018.01); *G16H 20/40* (2018.01); *G16H 50/00* (2018.01); *G16H 50/20* (2018.01); *A61M 60/148* (2021.01); *A61M 60/205* (2021.01); *A61M 2205/04* (2013.01); *A61M 2205/18* (2013.01); *A61M 2205/3303* (2013.01); *A61M 2205/3365* (2013.01); *A61M 2205/50* (2013.01); *A61M 2205/502* (2013.01); *A61M 2205/52* (2013.01); *A61M 2205/584* (2013.01); *A61M 2230/06* (2013.01); *A61M 2230/20* (2013.01); *A61M 2230/208* (2013.01); *A61M 2230/30* (2013.01); *A61M 2230/43* (2013.01); *G06N 5/045* (2013.01); *G06N 20/00* (2019.01)

(56) References Cited

FOREIGN PATENT DOCUMENTS

| | | |
|---|---|---|
| JP | 2014529308 A | 11/2014 |
| WO | 9843688 A1 | 10/1998 |
| WO | 2011115576 A2 | 9/2011 |
| WO | 2013003787 A2 | 1/2013 |
| WO | 2015160980 A1 | 10/2015 |

OTHER PUBLICATIONS

International Preliminary Report on Patentability and Written Opinion for Application No. PCT/US2018/067240 dated Jul. 2, 2020.
International Search Report for Application No. PCT/US2018/067240 dated Mar. 18, 2019.
Office Action from corresponding Japanese Application No. 2020-534212 dated Jan. 30, 2023 (17 pp.).
Office Action issued in corresponding Israeli Patent Application No. 275390 dated Jun. 8, 2023 (3 pp.).

SYSTEMS AND METHODS FOR PREDICTING PATIENT HEALTH STATUS

CROSS-REFERENCE TO RELATED APPLICATIONS

This application is a divisional of U.S. application Ser. No. 16/230,575, filed on Dec. 21, 2018, now U.S. Pat. No. 11,338,125, which claims priority to and the benefit of U.S. Provisional Patent Application No. 62/609,158, filed on Dec. 21, 2017, and entitled "SYSTEMS AND METHODS FOR PREDICTING PATIENT HEALTH STATUS". The entire contents of the above-referenced applications are incorporated herein by reference.

BACKGROUND

Acute and chronic cardiovascular conditions reduce quality of life and life expectancy. A variety of treatment modalities have been developed for heart health, ranging from pharmaceuticals to mechanical devices and transplantation. Temporary cardiac support devices, such as heart pump systems, provide hemodynamic support, and facilitate heart recovery. Some heart pump systems are percutaneously inserted into the heart and can run in parallel with the native heart to supplement cardiac output, such as the IMPELLA® family of devices (Abiomed, Inc., Danvers Mass.).

Currently, it is difficult or impossible for clinicians to track a patient's health status. Clinicians tend to rely on qualitative judgments and indirect estimates of cardiac function to predict a patient's health status, but these processes are inconsistent and unreliable. Determinations of a patient health status may vary between clinicians. Furthermore, the process is time-consuming for a clinician, and often a clinician is unable to analyze all of the measurements associated with the patient's cardiac function in time to make an informed health care decision.

BRIEF SUMMARY

The systems, devices, and methods described herein use predictive modeling to forecast patient outcome and keep track of patient condition over time, particularly relating to heart health for patients in cardiovascular distress and/or suffering from cardiogenic shock. In particular, the systems, devices, and methods enable heart pump systems to provide data useful for determining a probability of patient survival. One way to use the probability of patient survival is to rank a set of patients in order of lowest probability to highest probability, or may be used to assign the set of patients into different tiers for different ranges of probabilities of survival. In this manner, the systems and methods described herein are a quantitative and objective way to allow a clinician to identify the patients in the most dire condition, and direct his/her immediate attention to those patients who most need it. Another way to use the probability of patient survival to track an individual patient's probability of survival over a period of time, to provide a quantitative assessment of that patient's health over time. In this manner, the systems and methods provide a quantitative and objective way to allow a clinician to identify whether that patient's health is progressing as expected, so that the clinician may update the patient's treatment plan if needed.

The probability of patient survival may be determined at least based on one or more of a variety of factors including continuous and/or discrete measurements of heart performance acquired by the heart pump system. For example, one data parameter provided by the heart pump system may include cardiac power output (CPO). The CPO value may be used together with one or more clinical data parameters, such as lactate concentration measured from the patient, to determine the probability of survival, which may then be used to alter the operation of the heart pump system. Systems and methods of obtaining CPO and lactate concentration are described in detail below. One way to alter the operation of the heart pump system is to increase or decrease the level of cardiac support from the heart pump system, depending on the probability of survival. For example, if the probability of survival is high, the patient outlook may be good, and the heart pump system may decrease the level of cardiac support. Alternatively, if the probability of survival is low, the patient outlook may be worse, and the heart pump system may increase the level of cardiac support.

In some aspects, an intravascular heart pump system is inserted into vasculature of the patient. The heart pump system may be inserted using a minimally invasive procedure. For example, the heart pump system may be inserted via a catheterization through the femoral artery or vein. In some implementations, the heart pump system includes a cannula, a pump inlet, a pump outlet, and a rotor. For example, the intravascular heart pump system may be a percutaneous ventricular assist device, such as the IMPELLA® family of devices (Abiomed, Inc., Danvers Mass.). In some implementations, the rotor is coupled to a motor. The motor may drive the rotor and pump blood through the pump. In some implementations, the heart pump system includes one or more sensors. For example, the sensors may be configured to acquire data related to the heart pump system's performance, heart function, hemodynamic performance, or any other suitable data. In some implementations, the heart pump system includes a controller. For example, the heart pump system may include the Automated Impella Controller (AIC). The controller may be configured to execute instructions, analyze data, calculate values, determine relationships between parameters, or any other suitable task. For example, the controller may execute the methods described herein. The controller may comprise a processor, memory, a user interface, a display screen, a touch screen, user interactive buttons and/or dials, a power source, any other suitable element, or any combination thereof.

In some implementations, the heart pump system is positioned partially within the patient's heart. In some implementations, the heart pump system is a left ventricular assist device (LVAD). The heart pump system may be positioned within the patient such that the cannula extends across an aortic valve of the patient, the pump inlet is located within a left ventricle of the patient, and the pump outlet is located within an aorta of the patient. For example, the heart pump system may be inserted via a catheterization through the femoral artery, into the ascending aorta, across the aortic valve and into the left ventricle. In some implementations, the heart pump system is a right ventricular assist device (RVAD). For example, the heart pump system may be inserted through a catheterization procedure through the femoral vein and into the right atrium. Although some implementations presented herein are directed to heart pump systems implanted across the aortic valve and residing partially in the left ventricle, the same concept can be applied to devices in other regions of the heart, the cardiovascular system, or the body.

In some aspects, the systems and methods acquire first data related to time-varying parameters of a heart pump system, extract a plurality of features from the first data, and determine a heart health index. The heart health index may represent the health of the patient heart and may be indicative of the patient's cardiac performance as well as systemic perfusion leading to overall patient recovery and outcome. In some implementations, the heart health index represents a value indicative of a likelihood or probability of survival of the patient.

The systems, devices, and methods presented herein determine a heart health index and/or predict patient survival using measurements relating to a patient's health. In some implementations, the measurements are heart parameters related to cardiac function. In some implementations, the heart pump system takes, measures, processes, or otherwise quantifies the measurements.

The methods described herein may include acquiring first data or measurements related to time-varying parameters (such as any of the measurements described below) of a heart pump system. The first data may represent continuous or near-continuous measurements acquired via the heart pump system, or represent known quantities such as inputs to the heart pump system. The first data relates to operation of or factors measured by the heart pump system, and may include data indicative of heart rate, pump pressure, differential pressure, motor current, P-level, motor speed, any other data directly provided by, or inferred from data directly provided by, the heart pump system, or any suitable combination thereof. From these measurements, information about heart function, and in some cases information about the cardiac assist device performance (such as the occurrence of suction events, for example), can be determined. This information about heart function can be used in a predictive modeling system to predict patient outcome.

The first data may be determined from measurements obtained by one or sensors on the heart pump system, external systems, or both. For example, one or more sensors on the heart pump system may be positioned within the patient's heart, outside the patient's heart, or a combination of both, during operation of the heart pump system. In one example, sensors on the heart pump system measure pressure within the patient's vasculature. That pressure may be used in the calculation of additional parameters, such as cardiac power output, described below.

The methods described herein may include processing acquired or known data, such as the first data described above, to determine or estimate other parameters or features related to patient health or heart pump operation. In some implementations, these parameters are determined based in part on hysteresis between pressure measurements and motor current measurements that allow the detection of the phase of the cardiac cycle corresponding to a given pair of pressure and current measurements. In some implementations, multiple features are extracted from the first data. Extracting the features may include processing the first data at the heart pump system or at an external device. These may include left ventricular end diastolic pressure (LVEDP), stroke volume, ejection fraction, chamber distention, chamber hypertrophy, chamber pressure, stroke work, preload state, afterload state, heart rate, heart recovery, aortic pressure, differential pressure, motor current, motor speed, pump pressure, left ventricular pressure, end of diastolic pressure, aortic pulse pressure, native cardiac output, cardiac output, CPO, placement, mean flow, target flow, P-level, contractility, relaxation, a placement signal, average placement, standard deviation of placement, average placement range, standard deviation of placement range, average differential pressure, standard deviation of differential pressure, average differential pressure range, standard deviation of differential pressure range, left ventricular pressure maximum, left ventricular pressure minimum, pump pressure maximum, pump pressure mean, pump pressure minimum, differential pressure maximum, differential pressure minimum, motor current maximum, motor current minimum, motor current mean, motor speed mean, any other suitable feature related to heart function, and any combination thereof. The first data may be acquired during a first time period during which the heart pump system is in operation, such as a second, a minute, five minutes, ten minutes, an hour, a few hours, a day, a few days, a week, a month, or any suitable time frame. The average, mean, and minimum values of the features described above may be the average, mean, or minimum value of a feature during the first time period. The systems and methods described herein may use these plurality of features to determine a probability of survival or other heart health index of the patient, as described below.

In some implementations, the methods described herein include acquiring second data related to physiological parameters of the patient. The second data may be measured from the patient by a clinician or by a device external to the heart pump system, or may be inferred from measurements. The second data may include temperature, weight, height, waist size, body surface area (BSA), age, gender, urine output, creatinine level, potential of Hydrogen (pH), oxygen concentration, carbon dioxide concentration, lactate concentration, or any other suitable measurement or a patient sample, such as blood, urine, spit, plasma, feces, urine, tissue, or any other suitable sample. For example, a clinician may collect and analyze a blood sample from the patient to obtain the second data. In some implementations, the second data are acquired during the same time period during which the first data are acquired. The heart health index or probability of survival may be based on the second data.

The second data may be acquired through one or more sensors on the heart pump system and/or through external systems. The one or more sensors on the heart pump system and/or the external systems may be positioned within the patient's heart, outside the patient's heart, or a combination of both. For example, a clinician may measure a lactate concentration value in a patient's blood then input that lactate concentration into a user interface on the heart pump system or another system.

In some implementations, the heart pump system itself receives and processes both the first data related to cardiac function, as well as the second data related to physiological parameters. The heart pump system then calculates a heart health index or probability of survival as described herein. In other implementations, a device separate from the heart pump system, such as a computer, mobile device, tablet, or any other suitable device, receives the first data and the second data, and determines the heart health index or probability of survival based on that data, as described below.

In some implementations, the methods described herein include determining a heart health index indicative of the health of a patient's heart. The heart health index may be indicative of a likelihood of patient recovery, comprising a cardiac component and a systemic perfusion component. The cardiac component relates to a patient's heart health may include unloading, contractility, or any suitable indicator of a patient's heart performance. The system perfusion component relates to a patient's vasculature health and may include cardiac output (CO), aortic pressure mean (AoPm), or any suitable indicator of a patient's circulatory performance. In some aspects, the heart health index may be a probability of survival of the patient. Probability of survival is a value that is indicative of a likelihood of patient survival or expiration. In some implementations, the probability of survival is a numerical value, e.g., between 0 and 1. In some implementations, if the probability is greater than or equal to a threshold (e.g., 0.5) the probability of survival indicates survival (e.g., the patient has a greater than 50% chance of living given his or her heart health). The probability of survival may be based on the features described above. For example, a patient with low cardiac output, low maximum pressure, high minimum pressure a high standard deviation of differential pressure, or any suitable combination thereof may have a low probability of survival, while a patient with high cardiac output, high maximum pressure, low minimum pressure, a low standard deviation of differential pressure, or any suitable combination thereof may have a high probability of survival.

In some aspects, the method includes operating the heart pump system to treat the patient, such as actuating the pump, adjusting a level of support provided by the pump (such as by adjusting the motor speed to increase or decrease the level of support, for example), or de-actuating the pump. For example, if a patient has low CPO and high lactate concentration, the pump is actuated or turned on, or the level of support may be increased while the patient's health continues to be monitored. For a patient with high CPO and low lactate concentration, an already operating pump may be de-actuated or turned off, or the level of support may be decreased while continuing to monitor the patient's health.

In some implementations, a pump operating parameter value is selected based on the probability of survival. A pump operating parameter may be any factor affecting operation of the pump. For example, the pump operating parameter may be pump speed, P-level, motor current, target flow, or any other suitable parameter. In some implementations, pump speed is increased based on the heart health index, which may be the probability of survival (such as if the probability of survival is low or below some threshold). In some implementations, pump speed is decreased based on the heart health index (such as if the probability of survival is high or above some threshold).

The heart health index may be determined by using a prediction model. The prediction model may be a machine-learning model. For example, the prediction model may be one of: a logistic regression technique, a deep learning technique, a decision tree, a random forest technique, a naïve Bayes technique, and a support vector machines technique. The heart health index may be based on the plurality of features. The method may further include predicting, based on the heart health index, a patient outcome. In some aspects, the patient outcome may be expiration or survival of the patient.

The method may further include displaying the heart health index. For example, the heart health index may be displayed using a graphical user interface on the heart pump system or remotely on another system. The heart health index may be depicted as a numerical value, color representation, visual indicator, or any other suitable display method. For example, the AIC may display a green color if the probability of survival for the patient is greater than or equal to a first threshold, display a yellow color if the probability of survival is between a first threshold and a second threshold lower than the first threshold, and display a red color if the probability of survival is below or equal to the second threshold.

The method may further include acquiring a plurality of heart health indices. The heart health indices may include the heart health index, and each heart health index may correspond to a time period of a plurality of time periods. The method may further include determining, based on the plurality of heart health indices, a change in patient health. For example, small changes in a patient factor (e.g., CPO, contractility, motor current mean, etc.) may appear insignificant when viewed alone, but if viewed in combination with other patient factors may show an overall decline in patient health. These multiple factors can be accounted for in the heart health index. This method of aggregating multiple patient factors into a single value or trend allows a patient or clinician to quickly and easily interpret a patient's health. The method may further include displaying the plurality of heart health indices over the plurality of time periods. For example, the plurality of heart health indices may be displayed using a graphical user interface (e.g., on an AIC). For example, a clinician may view a graphical representation of heart health indices over time to easily visualize a trend in patient health. In some implementations, if the probability of survival of the patient is decreasing at a steady rate or decreasing at a rate above a given threshold, a clinician may be alerted to the patient's declining health. Such notification may include, for example, an auditory alarm, a flashing light on a user interface, an email or phone message, or any suitable notification. For example, a clinician may use the heart health index to determine quantitatively that a patient's probability of survival is decreasing steadily over the course of several days (or weeks). This determination would allow the clinician to intervene in the patient's care (such as by adjusting the operation parameters of the patient's heart pump) to improve the patient's outlook.

The method may further include displaying an indicator of a relative importance of a first feature of the plurality of features compared to a second feature of the plurality of features. This relative importance may be shown in a visual display. For example, each feature may be shown as a bar in a bar graph or as a point in a spider plot, with each bar or point in the plot given a size or placement relative to its importance. In some implementations, the heart pump system includes a controller including a user interface and a display screen. The relative may be displayed on the display screen. In some implementations, a clinician may be able to view the indicator remotely, e.g., through a personal computer or mobile device. For example, the controller may send a periodic report on patient status to a clinician, automatically or at the clinician's request.

In an embodiment, a method for measuring patient health status may include acquiring from a database a training dataset including a plurality of data points relating to time-varying parameters of a heart pump system. For example, the heart pump system's controller or a remote computer system may train on data obtained from multiple patient cases where patient outcome (e.g., survival or expiration) is known. The method may further include pre-processing the dataset to determine a plurality of features corresponding to the plurality of data points and processing the plurality of features to determine a pattern. For example, training the controller or computer system may include determining what patient factors had the greatest and least effect on patient outcome. The pattern may include a weight of each feature of a subset of the plurality of features. The method may further include acquiring patient data and calculating, based on the patient data and the pattern, the heart health index of a patient. By training a controller or computer system with known case data, the computer system can self-correct and "learn" how to accurately predict a patient's probability of survival.

In an embodiment, a heart pump system may include a catheter, a motor, a rotor operatively coupled to the motor, a pump housing, at least one sensor, and a controller. The pump housing may at least partially surround the rotor so that that actuating the motor drives the rotor and pumps blood through the pump housing. The controller may be configured to perform any of the methods described herein. For example, the controller may acquire, during a first time period and from the at least one sensor, first data related to time-varying parameters of the heart pump system; extract a plurality of features from the first data; determine, using a prediction model and based on the plurality of features, a heart health index indicative of the health of the patient's heart; and predict, based on the heart health index, a patient outcome.

In some aspects, an intravascular heart pump system, such as that described above or throughout the various embodiments described herein is inserted into vasculature of the patient. The heart pump system may be inserted using a minimally invasive procedure. For example, the heart pump system may be inserted via a catheterization through the femoral artery or vein. In some implementations, the heart pump system is positioned partially within the patient. In some implementations, the heart pump system is a left ventricular assist device (LVAD). The heart pump system may be positioned within the patient such that the cannula extends across an aortic valve of the patient, the pump inlet is located within a left ventricle of the patient, and the pump outlet is located within an aorta of the patient. For example, the heart pump system may be inserted via a catheterization through the femoral artery, into the ascending aorta, across the aortic valve and into the left ventricle. In some implementations, the heart pump system is a right ventricular assist device (RVAD). For example, the heart pump system may be inserted through a catheterization procedure through the femoral vein and into the right atrium.

In some implementations, the systems and methods described herein operate or are configured to operate the heart pump system during a first time period to provide a first level of cardiac support for the patient. For example, the heart pump system may operate at a first pump speed, P-level, or motor parameter, such as current delivered to the motor, power delivered to the motor, or motor speed. In some implementations, the system operates to provide a constant or near constant level of support to the patient.

In some implementations, the systems and methods described herein obtain at least one CPO value derived from measurements provided by the heart pump system. CPO represents cardiac pumping ability. CPO is a function of mean arterial pressure and cardiac output, where mean arterial pressure is a function of systolic blood pressure and diastolic blood pressure and cardiac output is a function of heart rate and stroke volume. Cardiac output can be estimated or measured through a variety of means, such as calculating the area under a volumetric pressure curve of a heart beat cycle for a patient. In some examples, CPO may be equal to mean arterial pressure multiplied by cardiac output and divided by 451. In some implementations, cardiac power index (CPI) is used instead of or in addition to CPO. CPI represents cardiac pumping ability normalized by body surface area. In some implementations, CPO is calculated from pressure measurements taken by one or more sensors of the heart pump system. In some implementations, obtaining the at least one CPO value includes determining cardiac output over time from sensors of the heart pump system. For example, a controller of the heart pump system may determine CPO from systolic, diastolic, and/or differential pressure measurements taken during operation of the pump system within the patient's vasculature. In some implementations, CPO is calculated every time a pressure measurement is updated at the sensor or the controller receives an updated pressure measurement. Alternatively, CPO may be calculated only when an updated pressure measurement is received that is different from a previous measurement by some amount. In some implementations, CPO is updated regularly at fixed time intervals following the first time period. For example, the first time interval may be 0.01 second, 0.1 second, 0.5 second, 1 second, 5 seconds 10 seconds, 1 minute, 10 minutes, 15 minutes, 30 minutes, 1 hour, or any suitable time interval.

In some implementations, the systems and methods described herein obtain at least one lactate concentration value measured from the patient. Lactate concentration represents the balance between lactate production and clearance in a patient. Lactate concentration may be measured via a patient's blood. For example, a clinician may measure lactate concentration by taking blood from a patient. In some implementations, the lactate concentration is manually input by a clinician or other user into a user interface connected to the heart pump system, or another device. In some implementations, the lactate concentration is imported via an electronic wired or wireless connection. For example, lactate concentrations for a patient may be stored in a remote storage location that communicates with the heart pump system to provide physiological parameter values for processing. In some implementations, the lactate concentration value is updated regularly at fixed time intervals following the first time period. For example, the second time interval may be 1 hour, 3 hours, 5 hours, 7 hours, 10 hours, 1 day, 1 week, or any suitable time interval.

In some implementations, the systems and methods described herein determine a prediction of patient outcome. The patient outcome may be based on the at least one CPO value and the at least one lactate concentration value. In some implementations, the prediction value of patient outcome represents a likelihood of patient survival or expiration. For example, the prediction value of patent outcome may be a value between zero and one, where one represents a high likelihood of patient survival and zero represents a low likelihood of patient survival.

In some implementations, the systems and methods described herein operate the heart pump system to treat the patient. For example, the pump operation may be altered based on the prediction value of patient outcome. In particular, altering the pump operation may include adjusting the operating parameters of the heart pump system to provide a second level of cardiac support during a second time period following the first time period. The second level of cardiac support may be the same as the first level of cardiac support, or the second level of cardiac support may be different from the first level of support. In one example, adjusting the operating parameters of the heart pump system includes adjusting pump speed (such as by increasing or decreasing, for example) based on a change in cardiac power output, lactate concentration, or both. It may be desirable to increase pump speed when the at least one CPO value is below a first threshold, when the at least one lactate concentration value is above a second threshold, or both. For example, the first threshold may be a value such as 0.3, 0.4, 0.5, 0.6, 0.7, 0.8, 0.9, 1.0 W and the second threshold may be a value such as 1, 2, 3, 4, 5, 6, 7 mmol/L. A low CPO value and a high lactate value may indicate the patient has a relatively low probability of survival. Because the patient is not doing well, the clinician may attempt to increase the level of cardiac support provided by the pump, by increasing the pump speed, for example. It may also be desirable to decrease or not change pump speed when the at least one CPO value is above the first threshold, when the at least one lactate concentration value is below the second threshold, or both. A high CPO value and a low lactate value may indicate the patient has a relatively high probability of survival. Because the patient is doing well, the clinician may decide to not change the parameters of the pump's operation. Alternatively, the clinician may attempt to reduce the level of cardiac support provided by the pump, or turn off the pump completely.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
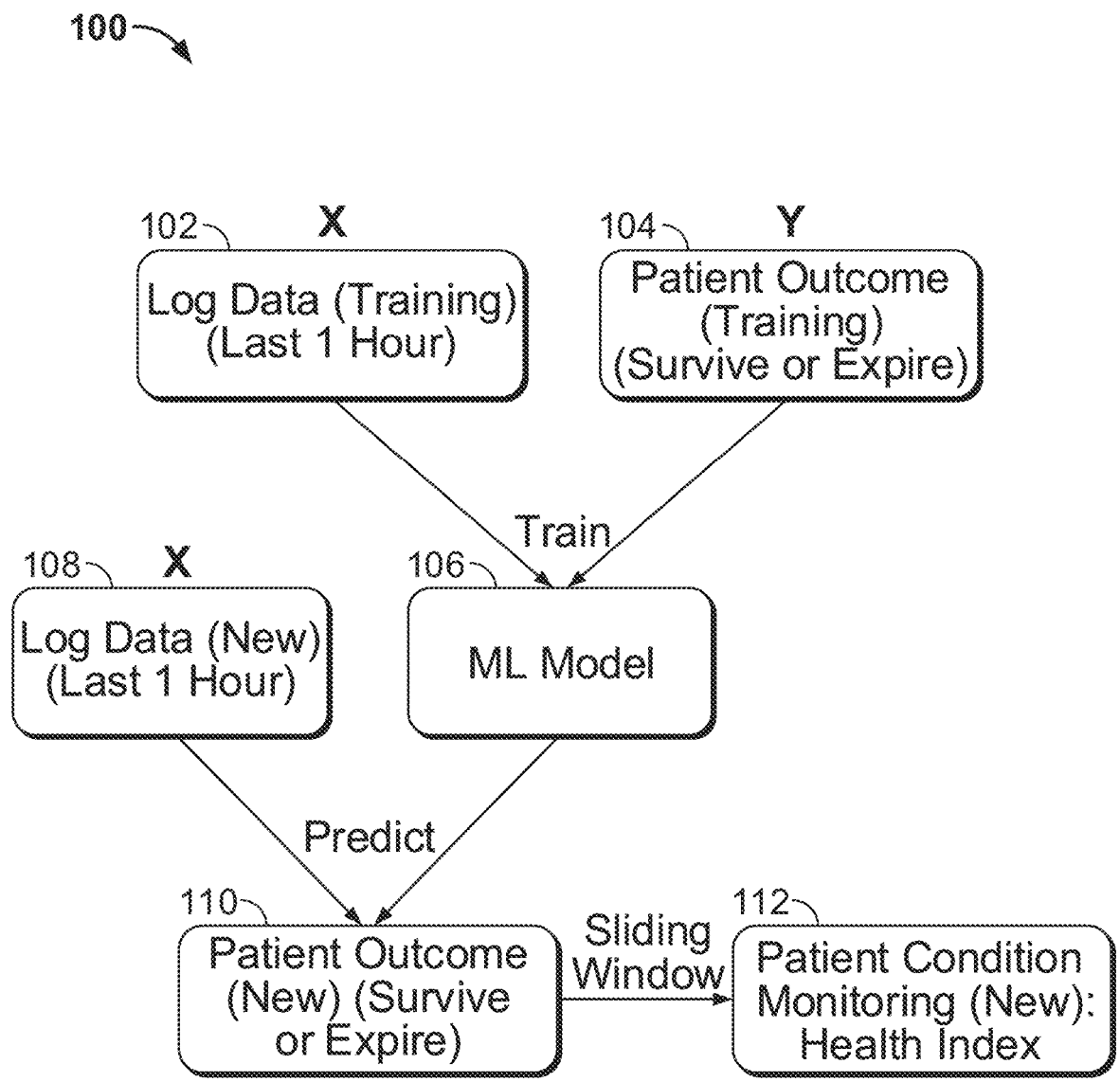
FIG. 1 shows a flowchart of a method for patient condition monitoring.

To provide an overall understanding of the systems, method, and devices described herein, certain illustrative embodiments will be described. Although the embodiments and features described herein are specifically described for use in connection with patient heart health, it will be understood that all the components and other features outlined below may be combined with one another in any suitable manner and may be adapted and applied to other types of medical therapy and patient health.

The systems, devices, and methods described herein use predictive modeling to forecast patient outcome and keep track of patient condition over time, particularly relating to heart health for patients in cardiovascular distress and/or suffering from cardiogenic shock. The forecasted patient outcome may based on a heart health index, which may be used interchangeably with health index throughout this description. The heart health index may include a cardiac component and a systemic perfusion component, and may be indicative of patient health. In particular, the systems, devices, and methods enable heart pump systems to provide data useful for determining patient outcome, or a probability of patient survival. The heart health index may be determined at least based on one or more of a variety of factors including continuous and/or discrete measurements of heart performance acquired by the heart pump system. For example, one data parameter provided by the heart pump system may include cardiac power output (CPO). The CPO value may be used together with one or more clinical data parameters, such as lactate concentration, to determine the patient's probability of survival, which may then be used to alter the operation of the heart pump system.

The systems and methods described herein also provide a classification model for patient outcome using cardiac parameters. There is an unmet need in the medical field to monitor patient health status through predictive modeling, particularly for patients with heart health problems, such as those who have been fitted with a heart pump system. Existing predictive modeling systems generally relate to physiological data but do not take into account the effects of a heart pump system implanted in the patient that could affect the patient's health, nor do existing modeling systems consider the data provided by such implanted heart pump systems. Moreover, these systems do not provide a solution for monitoring patient health status over time, or helping clinicians determine which patients most need immediate attention.

The systems and methods described herein may rely on data relating to the patient's heart pump system operation, such as motor current to the pump, in addition to physiological data measured by the heart pump system or from other sources, to predict patient outcome. Such physiological data may include age, gender, body size area (BSA), and clinical values such as lactate concentration, urine output, creatinine level, pH, concentration of $O_2$, and concentration of $CO_2$. Physiological data and other features used to predict outcome may be manually entered into the systems described herein or pulled automatically through electronic medical records.

The systems and methods described herein improve a clinician's ability to quantitatively and objectively determine the heart health of the patient by incorporating already available data when predicting patient outcome. By predicting a patient's probability of survival, the system may alert a clinician to a patient health problem before it would otherwise be detected, thereby providing the clinician with more time to treat the patient than the standard of care. For example, a patient's health may be slowly declining but the changes to individual features (e.g., heart rate, CPO, stroke volume, etc.) monitored by the clinician may be negligible or subtle enough not to alarm the clinician; the heart health index, however, may collate these seemingly insignificant changes and clearly represent an overall decline in patient health. By representing multiple features within a single metric, the heart health index provides an indicator of patient health that the clinician can easily interpret in an efficient manner. If the heart health index or probability of survival falls below a threshold or is rapidly decreasing, a clinician may be notified of the patient's failing health and may be able to treat the patient in a prompt manner. Moreover, the prediction of a patient's probability of survival may be used to rank a set of patients, or sort the patients into tiers for different ranges of probabilities of survival. In this manner, the clinician can quantitatively and objectively identify those patients who most need his immediate attention. This is also an improvement over the standard of care, in which clinicians may simply do rounds on their patients, in no particular order.

The operation of the heart pump system may be altered based on the heart health index or predicted patient outcome. One way to alter the operation of the heart pump system is to increase or decrease the level of cardiac support from the heart pump system, depending on the probability of survival. For example, if the probability of survival is high, the patient outlook may be good, and the heart pump system may be updated to maintain or decrease the level of cardiac support, or the clinician may even attempt to de-actuate the heart pump. Alternatively, if the probability of survival is low, the patient outlook may be poor, and the heart pump system may increase the level of cardiac support. The heart pump system may automatically adjust operation of the pump, or a clinician may manually adjust operation of the pump.

In some embodiments, the system trains a machine learning technique (classification model) to fit patient physiological signals with the label of patient outcome (survival or expiration). Patient physiological signals may include cardiac parameters such as aorta pressure, differential pressure, left ventricular pressure or any suitable signal derived from a physiological measurement from a patient. Features are extracted from the signals and used in the classification model. Suitable features may include, for example, a statistic of the physiological signal over a time period, such as a mean or a standard deviation of the raw signal. The classification model is used to classify patients with high or low risk and can be used to keep track of the patient's condition over time. The classification model may be a logistic regression technique, a deep learning technique, a decision tree, a random forest technique, a naïve Bayes technique, support vector machines, or any suitable model. The methods and systems described herein use the model to predict the patient's health status (e.g., the survival probability) using the previous window of signals to represent patient status in real time. Such systems and methods allow a user (such as a clinician or caregiver, for example) to track patient health status or health index and view changes to the outcome predicted for a patient, so that "risky" patients (such as patients with decreasing health indexes) can receive more careful attention. For example, the health status may be displayed on an interface that is connected to or is part of a heart pump system like the Automated Impella Controller (AIC). Raw features may be extracted from heart pump system signals. Such features may include the average or standard deviation of raw signals such as aortic pressure, differential pressure, and left ventricular pressure. Feature engineering can be used to find trends, to find jumps in signals, and to generate signals such as contractility from these raw signals.

FIG. 1 shows a flowchart of a method 100 for monitoring patient condition. The method shown in FIG. 1 may determine a heart health index as described above. At step 102, a system acquires training log ("X") data for a period of time. The period of time may be one hour (as depicted in FIG. 1), two hours, one day or any suitable length of time. Log data X may correspond to the most recent period of time of a plurality of periods of time for patient condition monitoring. At step 104, the system acquires training patient outcome ("Y") data. Patient outcome data associates a patient with survival or expiration. The patient outcome data may be associated with the period of time of the log data, such that the patient outcome data is indicative of the patient's status at the end of the period of time. Alternatively, the patient outcome data may not be associated with the period of time of the log data, and instead is indicative of the patient's status at a time after the end of the period of time. Log data X and patient outcome data Y are obtained from a large number N of patients, where N is large enough to adequately train a model for accurate prediction. Log data was measured and/or aggregated by one or more heart pump systems. The heart pump systems may be at least partially inserted within the heart of the N patients. For example, a heart pump system may extend across the patient's aorta into his or her left ventricle. The one or more heart pump systems may be the same or different type of heart pump system. Heart pump systems compatible with the present disclosure are disclosed in U.S. patent application Ser. No. 15/709,080 to Edelman et al. (U.S. Patent Publication No.: US 2018/0078159 A1, published Mar. 22, 2018), the contents of which are hereby incorporated by reference in their entirety. Generally, any other heart pump system or system for obtaining physiological data from a patient may be used with the present disclosure.

At step 106, the system builds a classification model, which may be a machine learning model. The model is trained on the training log data X and patient outcome data Y. The model may be stored in a database and may include mathematical rules for classification of features using a learning technique. A learning technique may be logistic regression, decision tree, deep learning, naïve Bayesian, or any other suitable technique.

For example, logistic regression is based on an equation used to represent the predictive model with coefficients learned from training data. A representation of the model may be stored in the database as a series of the coefficients, each corresponding to a weight indicative of a relative importance of a particular feature and can be used to calculate a probability, such as the probability of survival of a patient. Probability of expiration may be calculated as $(1+\exp(-x))^{-1}$, wherein x is equal to $\alpha*\text{Feature}\_\alpha + \beta*\text{Feature}\_\beta + \gamma*\text{Feature}\_\gamma + \ldots$ for any number of features and associated coefficients.

In another example, decision tree learning uses a decision tree as a predictive model to go from observations about an item to conclusions about the item's target value. Tree depth may be a hyper-parameter in decision tree learning. A hyper-parameter is a value that cannot be estimated from data used in the model. Hyper-parameters are often used to help estimate model parameters and can be tuned for a given predictive modeling problem. Precision may be used as a performance metric of a predictive model. By determining the maximum precision of the decision tree through tuning hyper-parameters such as tree depth, the system can provide an optimized machine learning model (such as machine learning model 106), and therefore better provide a prediction (such as patient outcome at step 110 described below). Receiver Operating Characteristic (ROC) and Area Under Curve (AUC) may also be used as metrics to compare prediction algorithms. In some implementations, steps 102, 104, 106, and any combination thereof are optional. For example, the method may start at step 108 described below. In some implementations, the classification model is updated periodically with new patient information. In some implementations, the classification model is collated, developed by, or run by a system separate from the heart pump system. For example, a third party system may collate data from multiple different heart pumps and build a machine learning model. That machine learning model, may in some examples, be used to enable steps 108 through 112.

At step 108, the system acquires new log data for a specific patient over the time period. The specific patient may be one of the N patients, for whom new log data was received, or may be a new patient not included in the N patients. At step 110, the new log data is input into the model trained at step 106, to predict patient outcome for the specific patient. Patient outcome may be a binary value representing survival or expiration.

At step 112, the model is used, along with the new log data, to predict the patient condition as a health index over time. In some implementations, the health index is displayed for patient monitoring. For example, the health index may be displayed on the heart pump system or may be viewed through a computer system, mobile device, tablet, or any other suitable device. The health index over time is found through a sliding window process. At a first time of a plurality of times, the health index is calculated for the specific patient over a time window. The health index is then calculated for the specific patient at a second time of the plurality of times, still over the time window. For example, at 2:00 pm the system may calculate the health index of Patient W, using the past one hour of log data (1:00 pm to 2:00 pm). At 2:15 pm the system may again calculate the health index of Patient W, using the past hour of log data (1:15 pm to 2:15 pm). As such, the window (the one hour time period) is "slid" across time in 15-minute increments to provide an updated, time-varying health index for the patient. The time in between calculations (15 minutes in the above example) may be any suitable time increment, such as one hour, half an hour, one minute, 20 seconds, etc. The health index may be a heart health indicator, indicative of the health of the specific patient's heart or a probability of survival. In some implementations, the health index is graphed over time and displayed to a clinician, so that the clinician may see the trend of the health index over time.

In some implementations, the health index includes a cardiac component and a systemic perfusion component. The health index may be indicative of overall patient recovery and probability survival (i.e., patient outcome). The cardiac component may include unloading, contractility, or any suitable indicator of a patient's heart performance. The system perfusion component may include cardiac output (CO), aortic pressure mean (AoPm), or any suitable indicator of a patient's circulatory performance.

Figure 2:
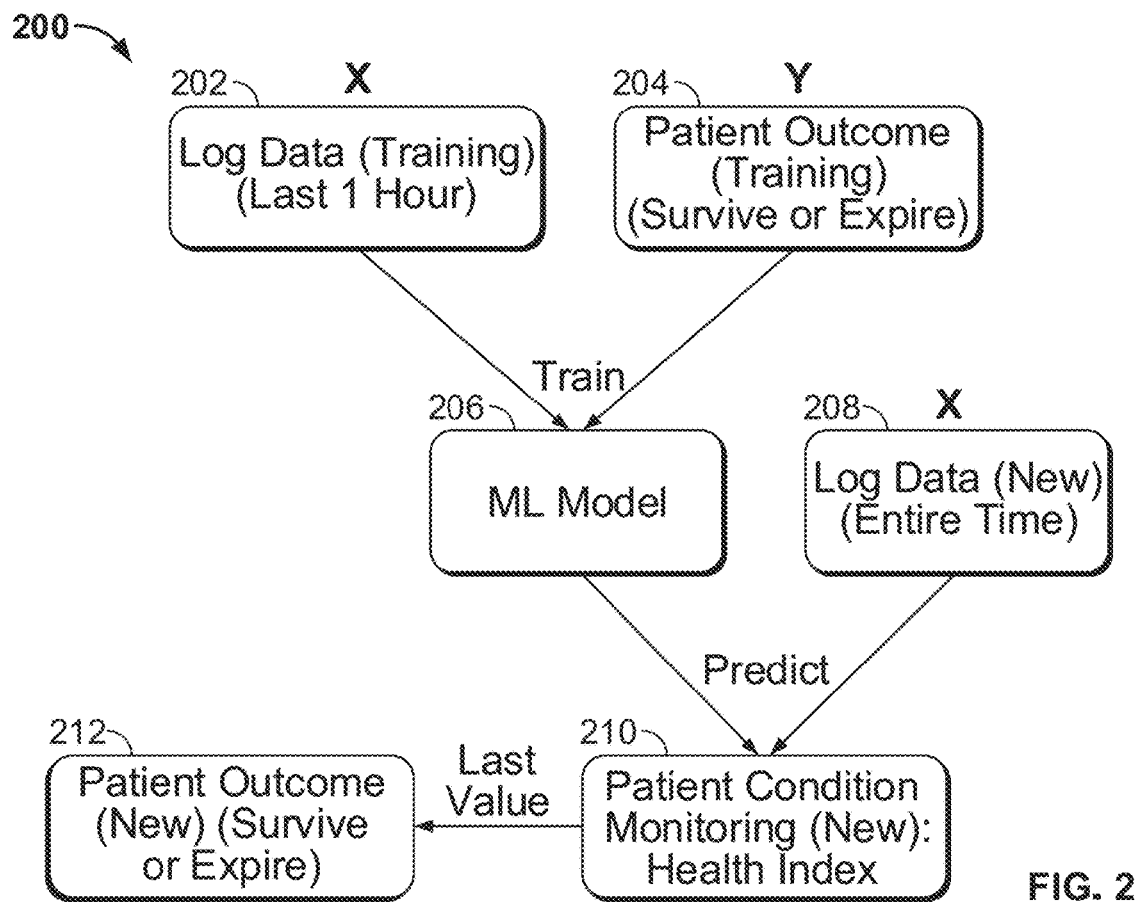
FIG. 2 shows a flowchart of a method for predicting patient outcome.

FIG. 2 shows a flowchart of a method 200 for predicting patient outcome through a method similar to that described in relation to FIG. 1. Steps 202, 204, 206, and 208 are identical to steps 102, 104, 106, and 108 from FIG. 1, respectively. Steps 202, 204, and 206 are optional; any combination of steps 202, 204, and 206 may be excluded from the methods described herein. For example, the model may already be developed or may be imported from an external system. At step 210, the model is used, along with the new log data to predict the patient condition as a health index over time. In some implementations, the health index is displayed for patient monitoring. The health index may be a heart health indicator, indicative of the health of the specific patient's heart or a probability of survival. At step 212, the health index is used to predict patient outcome. Patient outcome may be a binary value representing survival or expiration. For example, the health index may represent patient survival probability as a value x, where x is between 0 and 1 (inclusive). The health index may be used to determine a binary output. For example, if the health index is greater than 0.5 (or any other suitable threshold), the health index may indicate a patient outcome of survival, which corresponds to a binary value of one. This patient outcome may be displayed for a clinician. In FIG. 1, the system predicts patient outcome at step 110, then uses a sliding window to provide patient condition monitoring over time, at step 112. By contrast, in FIG. 2, the system uses the machine learning model and log data to provide patient health condition monitoring over time at step 210. The system then uses the last value calculated during patient condition monitoring (the health index) to provide a prediction of patient outcome at step 212.

Data used as the log data X or the patient outcome data Y described in relation to FIGS. 1 and 2 may be stored in a database system. The database system may include multiple databases or a single database. For example, the database may include a clinical data database, a device registry, and AIC logs. The database system may contain data for over thousands of cases. Each case may correspond to a separate patient or may correspond to an implantation of a heart pump system. The data may represent different case times and may come from time periods specific to each database within the database system. Features described by the data stored in the database system (for example, in AIC logs) may include pump type, pressure signal, P-Level, flow of a heart pump system, Impella flow, motor current, alarms, outcome or any other suitable feature. P-level is the performance level of the heart pump system and relates to flow control of the system. As P-level increases, the flow rate and revolutions per minute associated with the heart pump system increase. Data stored in a database system and the data stores contained therein may be used in training the models described herein.

The prediction modeling systems and methods described herein follow a data science approach by making predictions regarding a multitude of features using machine learning. Data science projects start with inputting data into a system. The data is pre-processed and feature engineered. Preprocessing challenges may arise when processing log data 102 and patient outcome data 104 of FIG. 1, prior to its use in training machine learning model 106. Challenges may include too many missing values and non-trustable data. Non-trustable data may include incorrect or incomplete data. An example of non-trustable data is when procedure outcome is listed as "expired" but the actual outcome at the end of intensive care unit (ICU) support is listed as "survived," within the database system. Incorrect data, incomplete data and a high proportion of missing data may each affect the performance of the predictive model. "Bad" data may be labeled as "non-trustable" data, "too many missing values" data, or any other type of label that indicates the data is untrustworthy and should be removed from the training data set or filled in to provide a better prediction of patient outcome and therefore improve patient health monitoring. Other examples of pre-processing may include data reformatting, removing unusable features, handling outliers, filling in missing values, encoding categorical features, scaling and any suitable step to resolve data issues. Once the raw data, such as log data 102 and patient outcome data 104 of FIG. 1, has been pre-processed, feature data may be extracted. Examples of feature data are shown in Table 1.

TABLE 1

| Cases # | Average Mean Placement Level | Std Mean Placement Level | Average Placement Range Level | Std Placement Range Level | Average Pdiffmean Level | Std Pdiffmean Level | Average PdiffRange Level |
|---|---|---|---|---|---|---|---|
| 1 | 74.1 | 32.34383 | 77.93333 | 105.7595 | 39.44167 | 44.7196 | 80.61667 |
| 2 | 84.08333 | 4.970887 | 44.71667 | 17.79896 | 29.90833 | 9.584054 | 109.3167 |
| 3 | 93.1 | 2.278157 | 55.06667 | 14.3479 | 36.01667 | 1.650673 | 84.6 |
| 4 | 63.93333 | 14.35255 | 68.5 | 53.44982 | 40.56667 | 24.161 | 99.7 |
| 5 | 83.65957 | 14.96987 | 147.1702 | 180.1325 | 49.39362 | 37.03634 | 149.3404 |
| 6 | 95.98333 | 49.22313 | 78.15 | 52.57624 | 32.60833 | 22.67691 | 137.25 |

| Cases # | Std PdiffRange Level | Average MeanFlow Level | Std MeanFlow Level | Average FlowRange Level | Std FlowRange Level | Average LVPMax Level | Std LVPMax Level |
|---|---|---|---|---|---|---|---|
| 1 | 87.38938 | 135.6833 | 61.04356 | 32.13333 | 27.63902 | 124.75 | 183.9011 |
| 2 | 26.25737 | 216.1667 | 51.2852 | 22.46667 | 12.8614 | 134.5833 | 25.91029 |
| 3 | 8.410707 | 142.3333 | 3.080404 | 22.76667 | 9.733733 | 132.3 | 14.84284 |
| 4 | 43.12938 | 216.5167 | 40.08719 | 15.48333 | 18.91163 | 123.1167 | 67.53495 |
| 5 | 79.82142 | 198.3404 | 59.23458 | 47.93617 | 41.5556 | 225.4681 | 170.5296 |
| 6 | 65.64618 | 154.5167 | 41.42 | 55.18333 | 31.71251 | 181.4833 | 117.1217 |

In some implementations, feature data is be split into training and cross-validation data, and used to build a machine learning technique. The machine learning technique may be applied to new, unclassified data to make a prediction on the new data, such as predicting a health status of a patient associated with the new data. The prediction, along with the feature data, may be further analyzed for visualization.

The systems and methods described in relation to FIGS. 1 and 2 and other processes described herein may use a portion or all of the data held in the database described above. For example, a machine learning technique may be trained using only the data stored in AIC logs.

Figure 3:
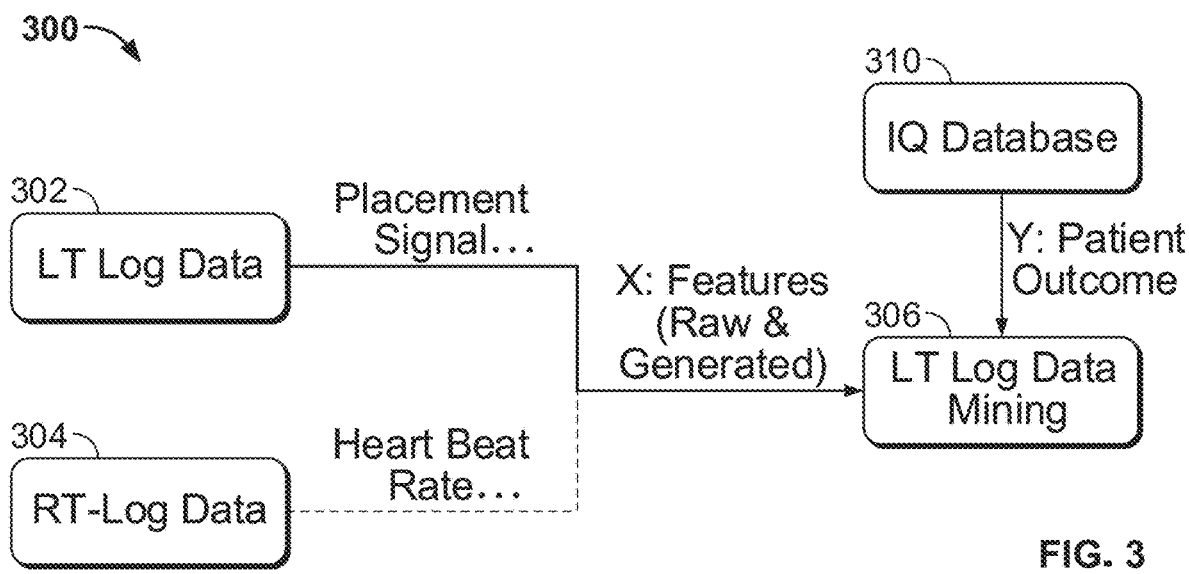
FIG. 3 shows a block diagram of log data mining.

FIG. 3 shows a data flowchart 300 for AIC log data, such as that held in AIC logs, described above in relation to a database system. Long term (LT) Log Data 302 has, for example, a placement signal. LT may correspond to one sample per minute or any other suitable sampling rate. Real time (RT)-Log Data 304 produces features such as a heartbeat rate, using information sampled at a sampling rate higher than the sampling rate corresponding to LT data. RT may correspond to 25 Hz (25 samples per second) or any other suitable sampling rate. The combination of LT Log Data and RT-Log Data is processed as raw and generated features that are then input to Log Data Mining 306 as X. IQ Database 310 contains patient outcome, which is also input to Log Data Mining 306 as Y. Log Data Mining 306 may be used to extract relevant and/or important features for use in training a machine learning model, such as machine learning model 106 of FIG. 1, and may therefore be used to provide a more efficient patient outcome prediction.

Figure 4:
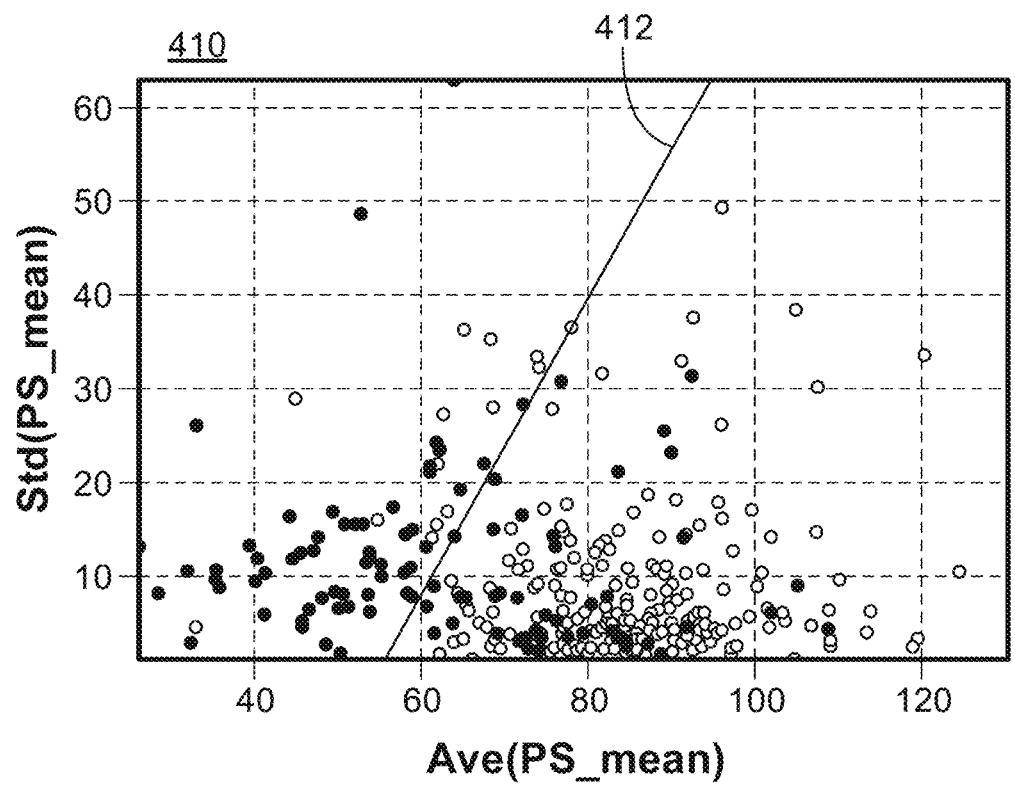
FIG. 4 shows two scatter plots with decision boundaries used for training and classification.
Figure 4:
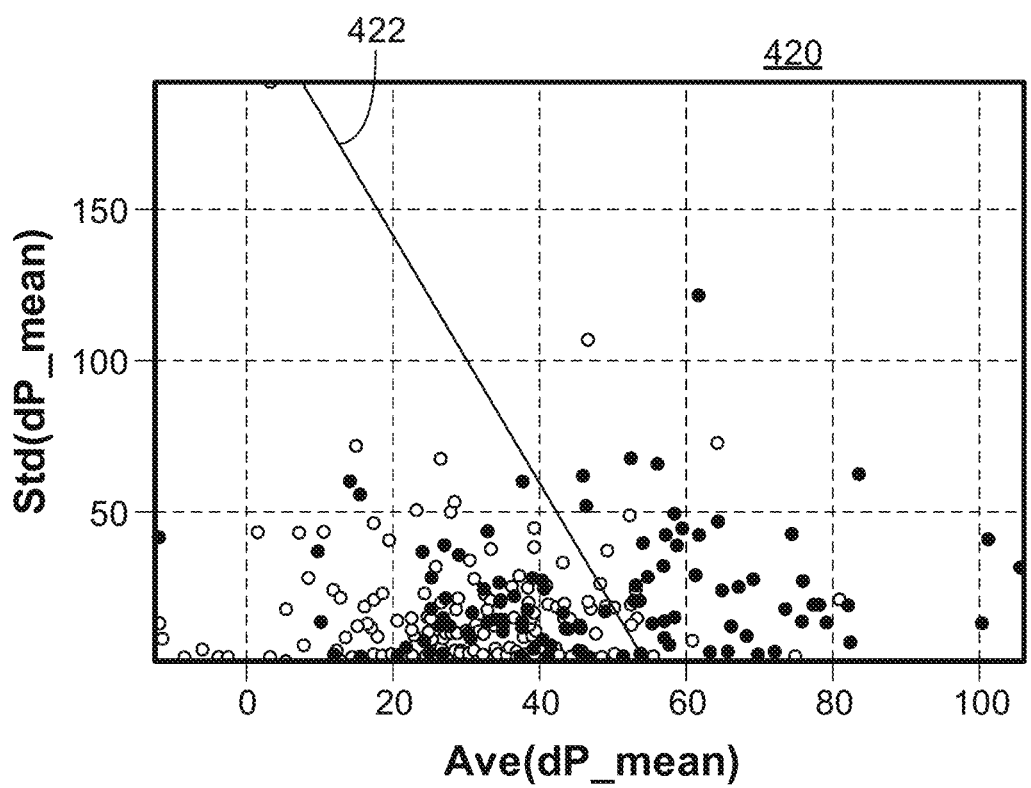
Figure 5:
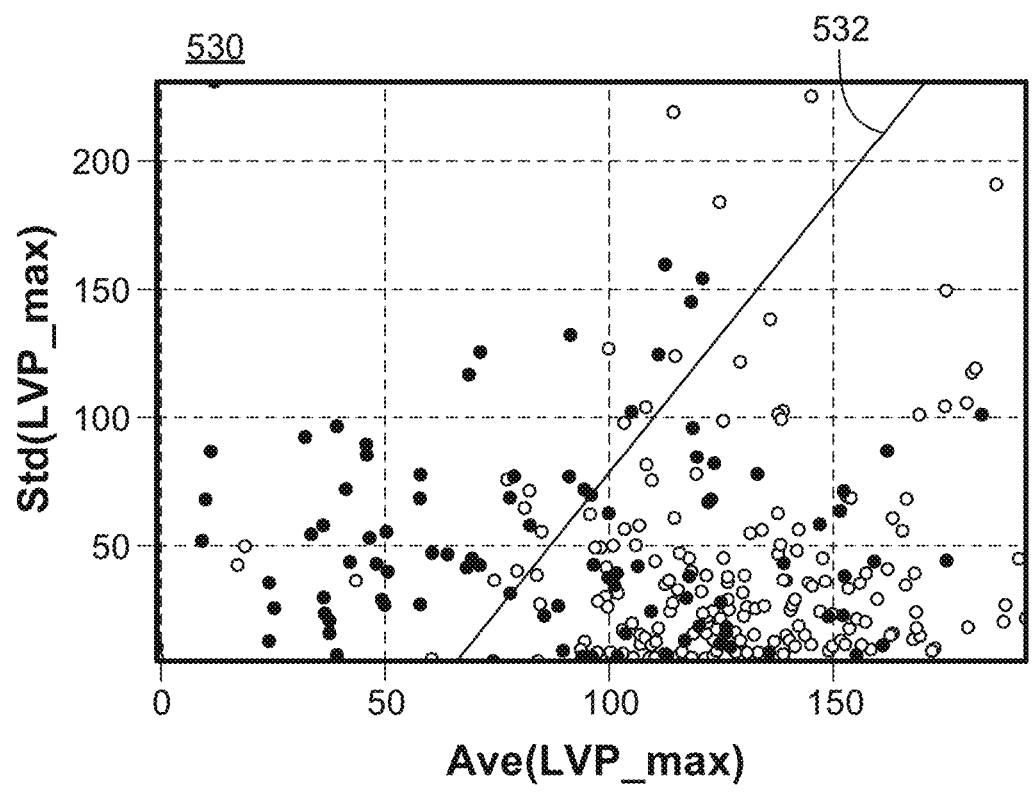
FIG. 5 shows two scatter plots with decision boundaries used for training and classification.

First data related to cardiac or heart pump parameters and/or second data related to physiological parameters, such as the first data and second data described above, may be used to predict a patient outcome. In some implementations, first data and/or second data for a plurality of patients is used to build a predictive modeling system, such as that described above in relation to FIGS. 1-3. First data and/or second data may be included in a modeling training set or for feature extraction as described above in relation to FIG. 3. The methods and systems described herein may test for any significant separation between two groups of data corresponding to patient outcome as a function of one or more patient parameters. For example, FIGS. 4-7 described below show two different patient parameters graphed against one another to determine if the parameters show a separation along patient outcome. Only a few examples are described herein, but such a test may be implemented for any number of patient parameters of first data and/or second data. Some data shown herein show significant separation, as shown in FIGS. 4-5. Paired parameters exhibiting significant separation (e.g., as represented by boundaries 412, 422, 532) may be more predictive regarding patient outcome, than other parameters. Other parameters showing less significant or no significant separation (e.g., as exhibited in FIGS. 6-7 described below) may be less predictive regarding patient outcome, than other parameters.

FIGS. 4 and 5 show example feature plots used for training and classification, for features that lend themselves to decision boundary separation. In graphs 410, 420, and 530 unshaded dots represent survival cases, while shaded dots represent expired cases. In each graph the machine learning result is represented by a linear decision boundary that is used to separate the shaded and unshaded dots with the best trade-off, using logistic regression. The dots, as a whole, represent patient outcome training data, such as data Y, described above in relation to step 104 of FIG. 1. Their placement within graphs 410, 420, and 530 is determined by the associated log data training, such as data X, described above in relation to step 102 of FIG. 1.

Graph 410 depicts a calculated boundary 412 for mean placement signal (PS), which can also be referred to as mean placement level. Placement signal may be aortic pressure for Impella CP/2.5 cases or differential pressure for Impella 5.0/LD cases. The x-axis of graph 410 represents the average of the mean placement signal (PS_mean), while the y-axis represents the standard deviation of PS_mean. For example, an unshaded dot may represent a patient who survived (from patient outcome training data 104). The patient is also associated with a set of mean placement level data (from training log data 102). The system may compute an average mean placement level and standard deviation of mean placement level for that patient and graph an associated unshaded dot, accordingly. Once the dots have been graphed for patients included in the training data, according to their average mean placement level and standard deviation of placement level, the machine learning model (such as machine learning model 106 of FIG. 1) calculates a linear decision boundary 412. The linear decision boundary may be represented by a series of a coefficients tied to the training data, as described above. When the system receives new data relating to a new patient (such as new log data 108 of FIG.

1), the system may determine the average mean placement and standard deviation of mean placement of the new patient. Depending on where these values "place" the patient's dot in graph 410, a predicted patient outcome may be determined based on the location of the dot relative to the decision boundary 412. For example, if the patient has an average mean placement level of 100 and a standard deviation of mean placement level of 30, the predicted patient outcome would be survival, according to graph 410. This is because the patient's dot would fall on the right side of boundary 410, and is therefore more strongly associated with patients who survived (unshaded dots). Such a calculation (where a new patient falls in relation to a decision boundary) may constitute a patient outcome prediction like that described in above in relation to FIG. 1. Thus the decision boundary may represent a threshold for predicting patient outcome. The decision boundary may be calculated differently in different machine learning instances. For example, in some instance decision boundary 412 may be shifted to the right or the left, may have a different slope, or may be non-linear.

Similarly, graph 420 depicts a calculated boundary 422 for mean differential pressure. The x-axis of graph 420 represents the average of mean differential pressure, while the y-axis represents the standard deviation of mean differential pressure.

Graph 530 depicts a calculated boundary 532 for maximum left ventricular pressure (LVP). The x-axis of graph 530 represents the average of maximum LVP, while the y-axis represents the standard deviation of maximum LVP.

Figure 6:
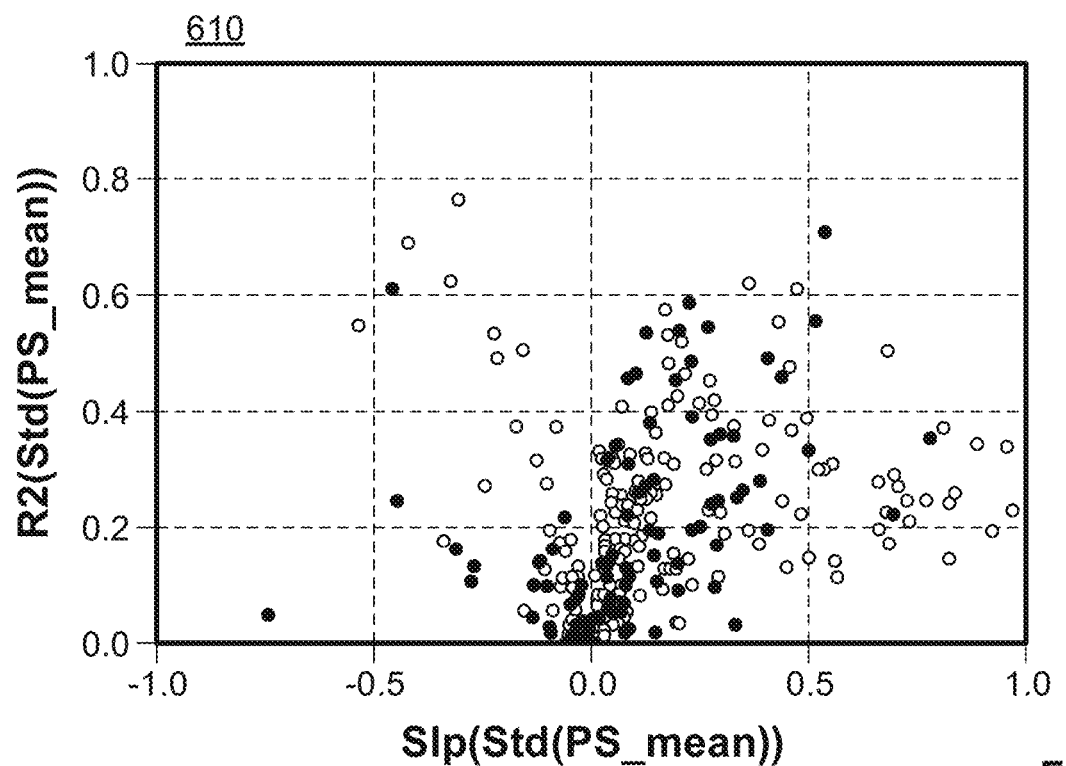
FIG. 6 shows a scatter plot that does not lend itself to decision boundary separation.
Figure 7:
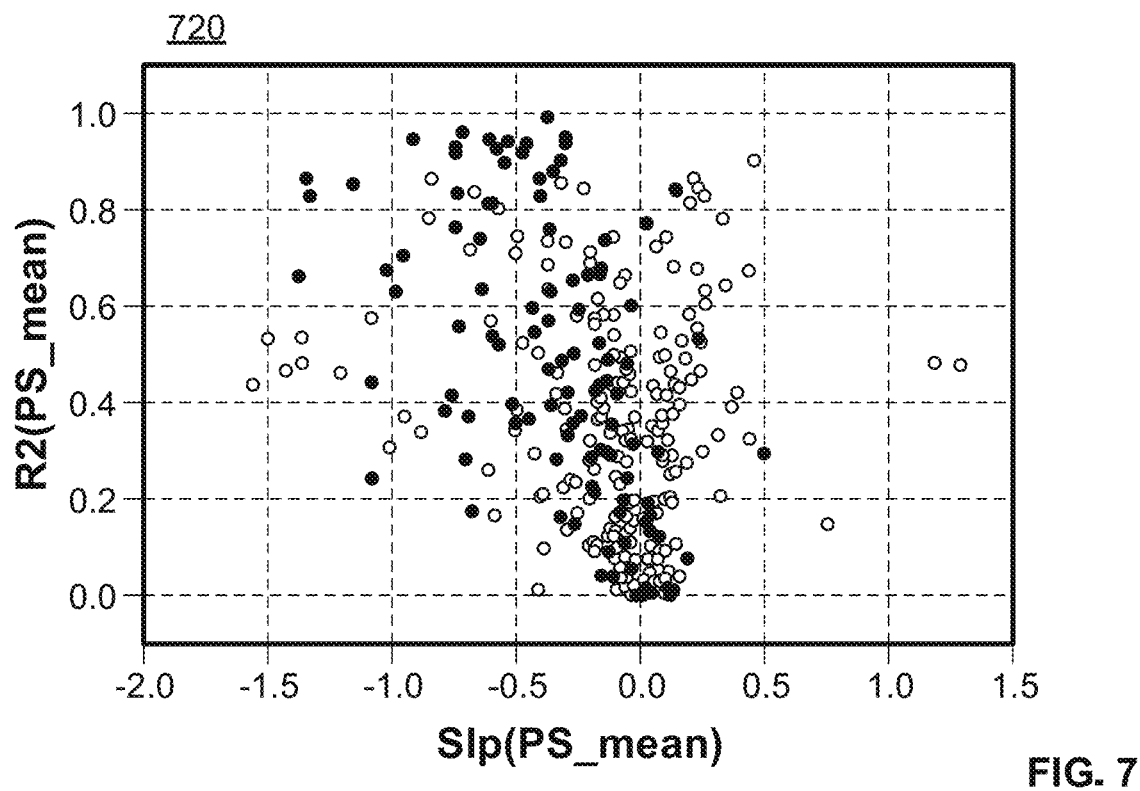
FIG. 7 shows a scatter plot that does not lend itself to decision boundary separation.

FIGS. 6 and 7 shows two example feature plots that do not lend themselves to decision boundary separation. In graphs 610, 720 unshaded dots represent survival cases, while shaded dots represent expired cases. Without a boundary separation, the information distributions shown by graphs 610, 720 may be less helpful than information distributions such as those shown in FIGS. 4 and 5 in predicting patient outcome, because the system is not provided with a clear boundary line (or equation with set of coefficients) with which to categorize new patient data. The x-axis of graph 610 represents slope of the linear regression of the PS_mean over time, while the y-axis represents the coefficient of determination (also known as r-squared or $r^2$) of the linear regression of PS_mean. The data represented in graph 610 is non-separable because the shaded and unshaded dots have the same pattern. The x-axis of graph 720 represents Slp (PS_mean), while the y-axis represents the coefficient of determination of linear regression of PS_mean. The data represented by graph 720 is semi-separable because the shaded and unshaded dots have different patterns but may be "weak" for separation.

Figure 8:
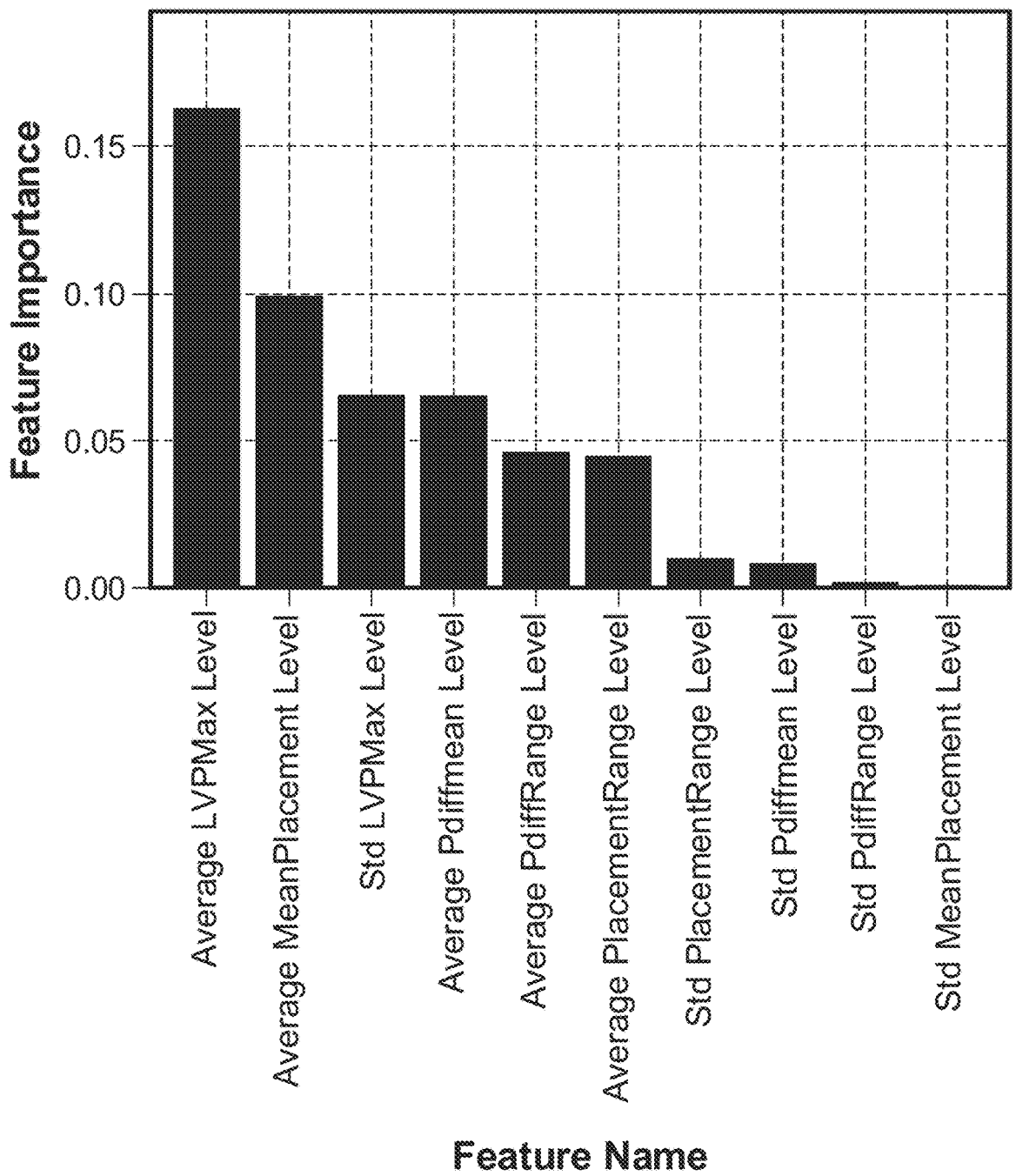
FIG. 8 shows bar graphs ranking feature importance.
Figure 8:
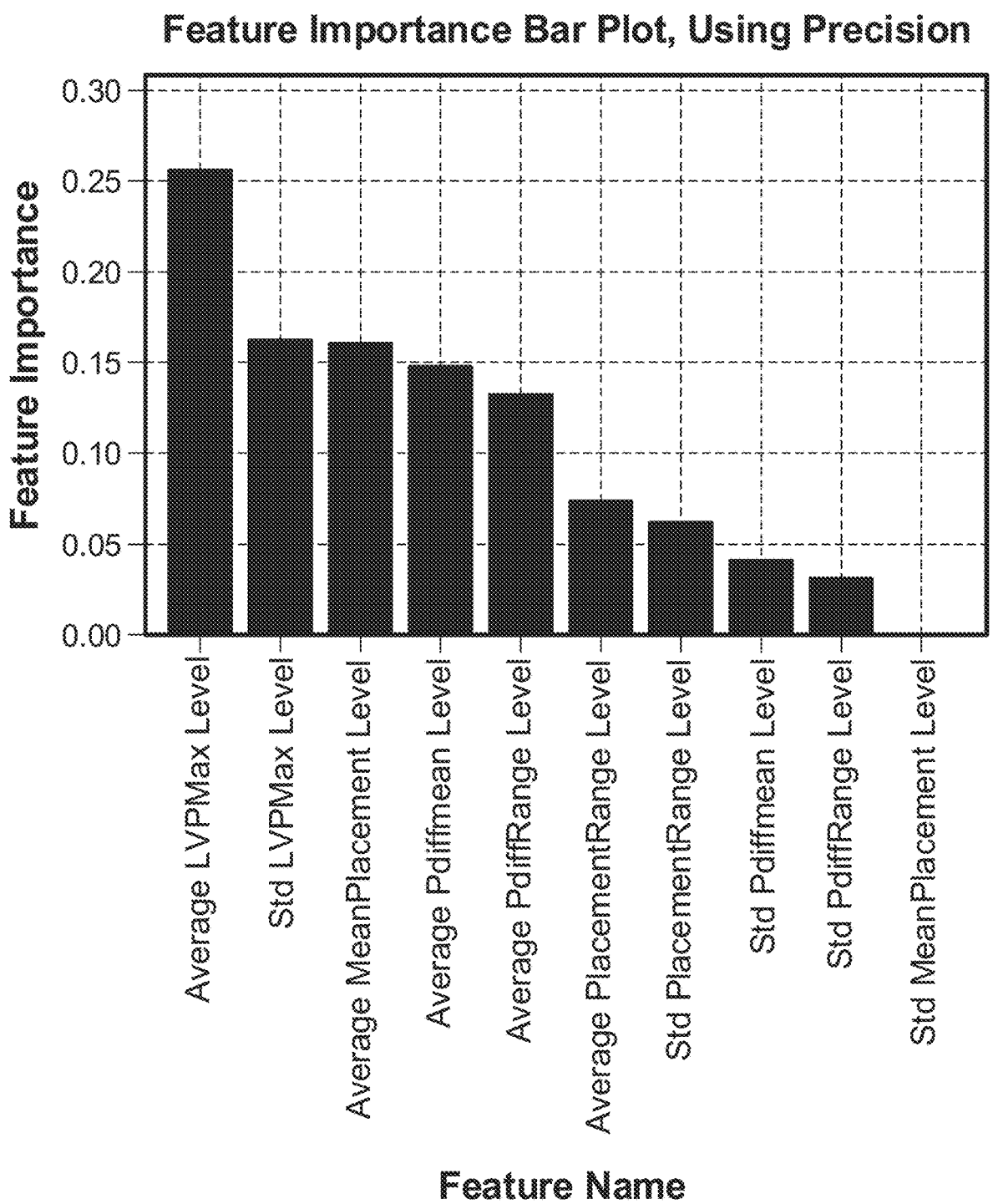
Figure 8:
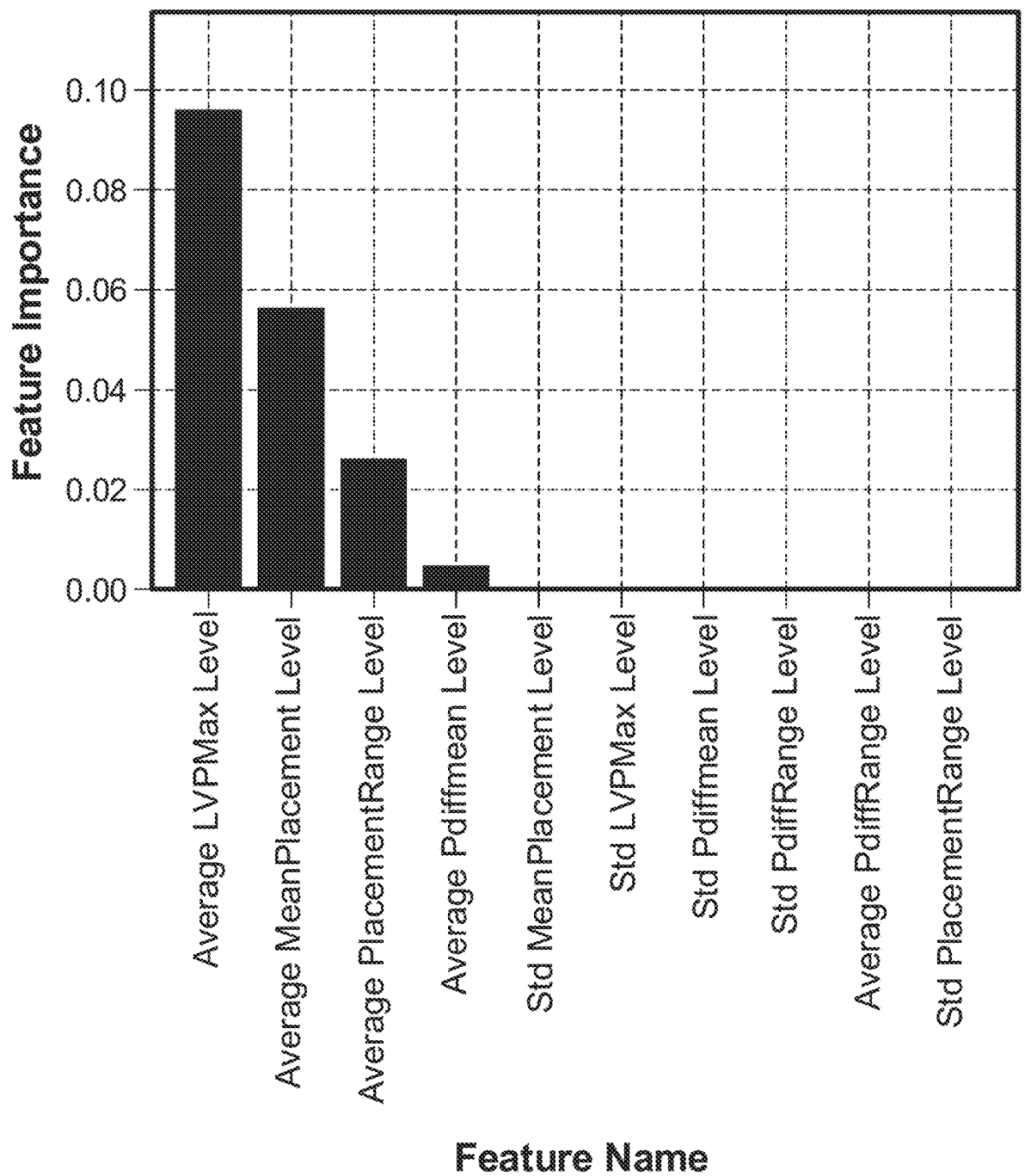

FIG. 8 shows example bar graphs ranking feature importance, as an example result of the machine learning techniques described herein. The feature importance may correspond to coefficients of a logistic regression model used, for example, as the machine learning model 106 of FIG. 1 to predict patient outcome. A higher coefficient in the model may correlate to a higher importance of a feature to overall patient health. Knowing the feature importance may be especially helpful for clinicians when determining a method of treatment in response to a decline in patient heart health (as may be exhibited by patient condition monitoring 112 of FIG. 1). Generally, features may include aortic pressure, differential pressure, motor current, left ventricular pressure, end of diastolic pressure, aortic pulse pressure, native cardiac output, cardiac output, CPO, placement, flow, P-level, contractility, and relaxation. These features may be processed to determine additional features such as average placement, standard deviation of placement, average placement range, standard deviation of placement range, average differential pressure, standard deviation of differential pressure, average differential pressure range, standard deviation of differential pressure range, left ventricular pressure maximum and left ventricular pressure minimum. Importance of these features may be determined by ranking the features using different calculations.

Graph 810 shows feature ranking using F-1. F-1 is a statistical term defined as 2*precision*recall/(precision+recall). Precision equals TP/(TP+FP) and recall equals TP/(TP+FN), where in TP represents true positive, FP represents false positive and FN represents false negative. Graph 820 shows feature ranking using precision. Graph 830 shows feature ranking using recall. In all three graphs 810, 820, 830 the most important feature (the feature with highest importance) is average LVP maximum level, suggesting that this feature is useful in understanding a person's health status, compared to other features shown in FIG. 8. In graphs 810 and 830, average mean placement level is ranked as the second most important feature. However, in graph 820 average mean placement level is ranked third. The differences in feature rankings between graphs 810, 820, 830 show that the different metrics (such as precision, recall, or F-1 score) used to calculate the feature importance can affect the outcome of what features are deemed most important and are given the most weight in the model.

Figure 9:
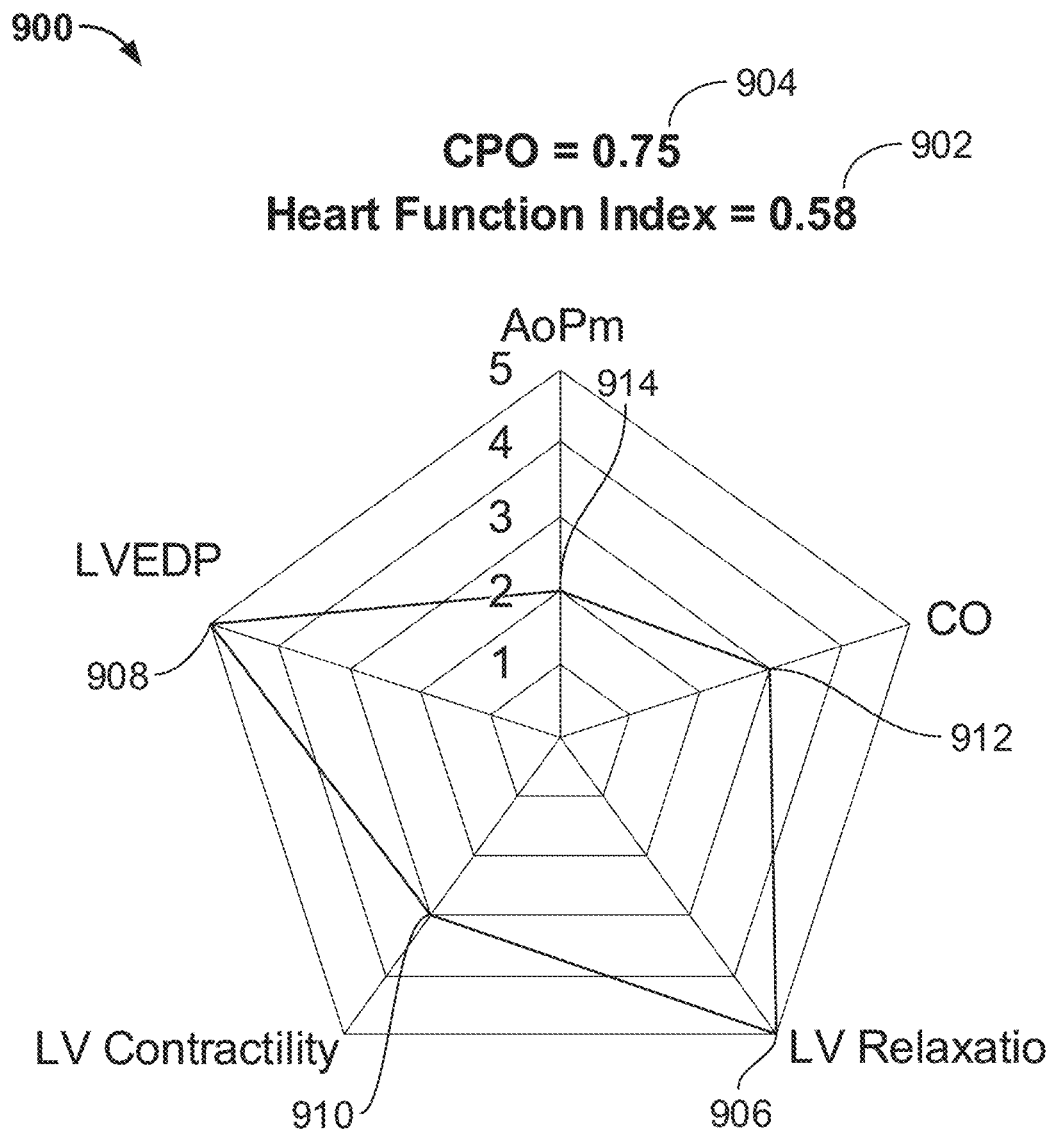
FIG. 9 shows a spider plot showing feature rating.

Displaying a visual representation of feature importance may be helpful to clinicians. A graphical representation may allow a clinician to more quickly or easily interpret feature importance, when compared to a numerical display. Specifically, feature importance may be represented through a bar graph as depicted in FIG. 8 or through a spider plot as depicted in FIG. 9. In some implementations, a visual representation shows the patient's health condition and/or feature importance at a single point in time or an average over multiple points in time. In some implementations, the visual representation is updated periodically, at regular intervals, or in real time, such that the visual representation appears to a viewer as a video stream.

FIG. 9 shows an example spider plot 900 showing relative feature rating for a patient. The heart function index 902 of the patient is 0.58 in this case, and is an example of a heart health indicator, as described above. The CPO 904 associated with the patient is 0.75. CPO is a function of mean arterial pressure (MAP) and CO. CPO may be used as a predictor for patient outcome and may be a component of a heart health indicator. FIG. 9 shows patient features and ratings at a single point where the CPO was 0.75 and the heart function index was 0.58. These values could be updated over time. In one example, CPO may be a time-varying feature used in calculating the likelihood of patient survival.

Spider plot 900 visually displays the relative effect of five features on the patient's health. Each feature is given a rating, representing the status of the feature for the patient on a scale of one to five. In some implementations, the rating is on another scale, such as zero to one, one to ten, one to fifty, one to one hundred, one to one thousand, or any other suitable scale. A left ventricular (LV) contractility rating of 1 indicates a dP/dt (which may be a ventricular contractility assessment) max greater than 200 mmHg/sec, a rating of two indicates greater than 400 mmHg/sec, a rating of three indicates greater than 600 mmHg/sec, a rating of four indicates greater than 600 mmHg/sec, and a rating of five indicates greater than 1000 mmHg/sec. A LVEDP rating of one indicates a deviation by 20 mmHg, a rating of two indicates a deviation of 15 mmHg, a rating of three indicates a deviation of 10 mmHg, a rating of four indicates a deviation by 5 mmHg, and a rating of five indicates LVEDP in the target range of 10-15 mmHg, where deviation is measured as the deviation from this target range. An LV relaxation rating of 1 indicates a dP/dt max less than 1000 mmHg/sec, a rating of two indicates less than 800 mmHg/sec, a rating of three indicates less than 600 mmHg/sec, a rating of four indicates less than 400 mmHg/sec, and a rating of five indicates less than 200 mmHg/sec. An AoPm rating of one indicates 60 mmHg, a rating of two indicates 70 mmHg, a rating of three indicates 80 mmHg, a rating of four indicates 90 mmHg, and a rating of five indicates 100 mmHg. A CO rating of one indicates a CO of 2 L/min, a rating of two indicates 3 L/min, a rating of three indicates 4 L/min, a rating of four indicates 5 L/min, and a rating of five indicates 6 L/min, where the measurement of CO is a function of heart beat and stroke volume. For example, LV relaxation 906 is five, LVEDP 908 is five, LV Contractility 910 is three, CO 912 is three, and AoPm 914 is two. In this instance, AoPm is low relative to the other features and therefore the AoPm of the patient is worse relative to the other features of the patient. Displaying feature data in this manner, and on a uniform rating scale across features, allows a clinician to quickly view the patient data and perceive which features may need to be addressed to improve the overall health of the patient. In this instance, a clinician may look at spider plot 904 and decide to first address the patient's AoPm. After addressing the patient's AoPm through clinical means, a clinician may then observe, through patient condition monitoring (step 112 of FIG. 1) and on spider plot 904, updated patient heart health status in time and may track progress of the patient.

The features displayed in spider plot 904 may be weighted due to their relative feature importance. For example, CO may have a weighting of 0.4, LV contractility may have a weighting of 0.2, LVEDP may have a weighting of 0.3, AoPm may have a rating of 0.2 and LV relaxation may have a weighting of 0.1. In this example, though AoPm may still have the lowest un-weighted rating, CO may have the lowest weighted rating, because of its relative importance and low rating. In another example, the features may be weighted equally.

Figure 10:
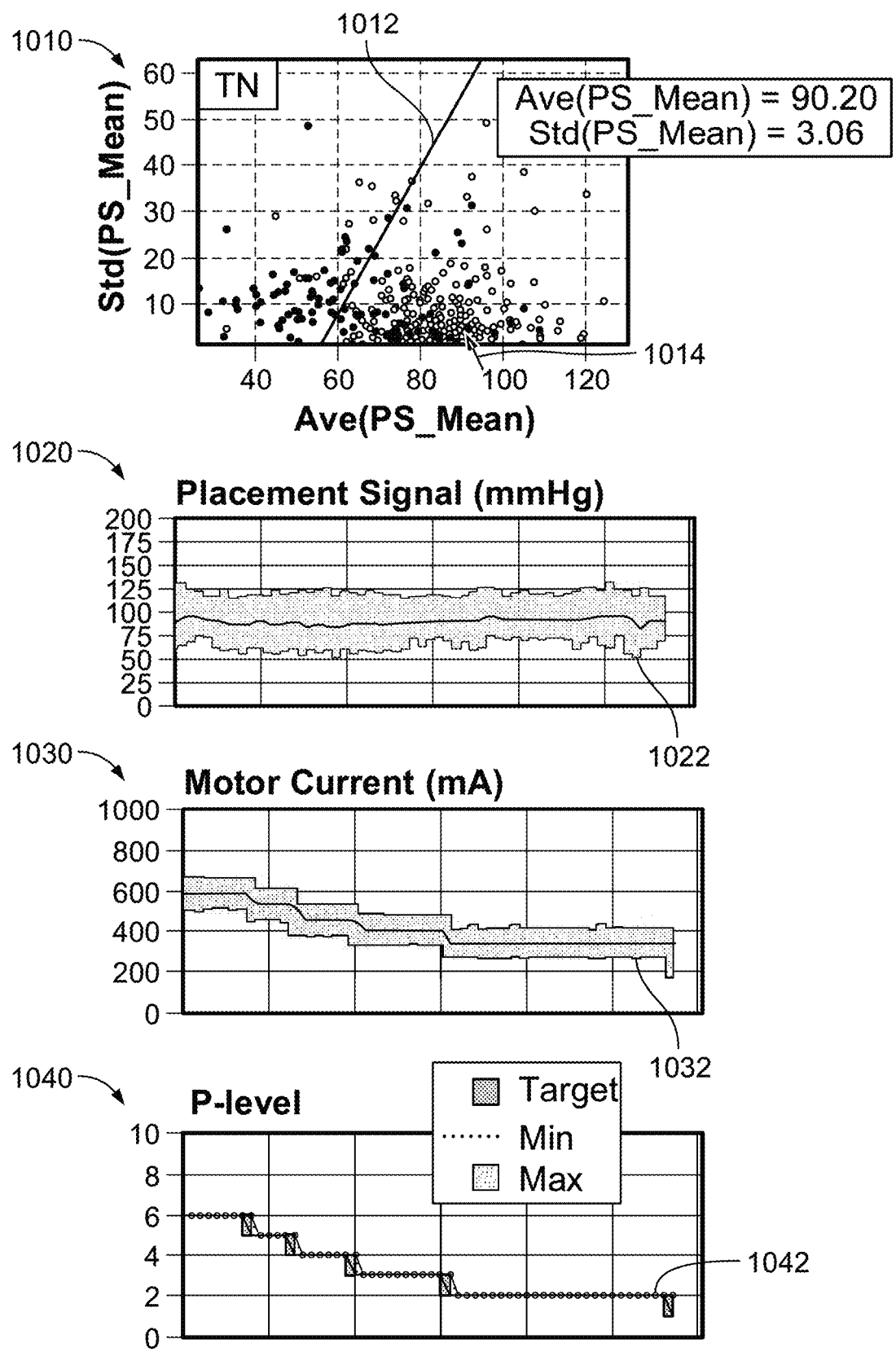
FIG. 10 shows an example of features of a specific patient, Patient X.

FIG. 10 show an example of features of a specific patient, Patient X. Graph 1010 shows a decision boundary 1012. As described above, an unshaded dot represents survival of a patient, while a shaded dot represents expiration of a patient. Dot 1014 represents Patient X, who survived. Accordingly, dot 1014 is located to the right of decision boundary 1012, as described above. Decision boundary 1012 may represent a line between when a patient is more likely to survive or expire. For example, patients to the right of boundary 1012 may be more likely to survive while patients to the left of boundary 1012 may be more likely to expire. The x-axis of graph 1010 represents the average of mean placement signal (PS), while the y-axis represents the standard deviation of mean PS. FIG. 10 shows one example a user interface for the clinician when the clinician interprets the patient's heart health by investigating placement signal, motor current, P-level, and likelihood of survival. Specifically, graph 1010 allows the clinician to see a graphical representation of the patient's likelihood of survival in relation to a boundary between the standard deviation and average of placement signal. For example, graph 1010 allows a clinician to visualize a distance between the boundary 1012 and data representative of the patient 1014. That distance from a boundary or separation line may show a clinician how likely a patient is to survive. For example, a patient far to the right of decision boundary 1012 (e.g., a patient with high average placement signal) may be more likely to survive than a patient closer to the decision boundary (e.g, a patient with lower average placement signal).

Graph 1020 shows placement signal 1022. The y-axis of graph 1020 represents pressure in mmHg. Graph 1030 shows motor current signal 1032. The y-axis of graph 1030 represents motor current in mA. Graph 1040 shows P-level 1142. The y-axis of graph 1040 represents P-level. The x-axes of graphs 1020, 1030, 1040 represent time. Graphs 1020, 1030, 1040 are shown for the same time period, at the same time scale, for the same patient, Patient X, represented by dot 1014. Placement signal 1022, motor current signal 1032, and P-level 1042 may be indicative of first data related to time-varying parameters of the heart pump system, as described above. Placement signal 1022, motor current signal 1032, and P-level 1042 may be features of a plurality of features used to determine a heart health index for a patient. In some aspects, the heart health index may be a probability of survival of the patient, which may be used to predict a patient outcome. In this case, the patient outcome (represented by for 1014) is survival. As shown in graph 1040, P-level is gradually decreased over time. In one example, a clinician may view the Patient X's likelihood of survival to determine when and by how much to change the P-level. In the example shown in FIG. 10, the P-level is stepped down incrementally, thereby decreasing the speed of the pump.

Figure 11:
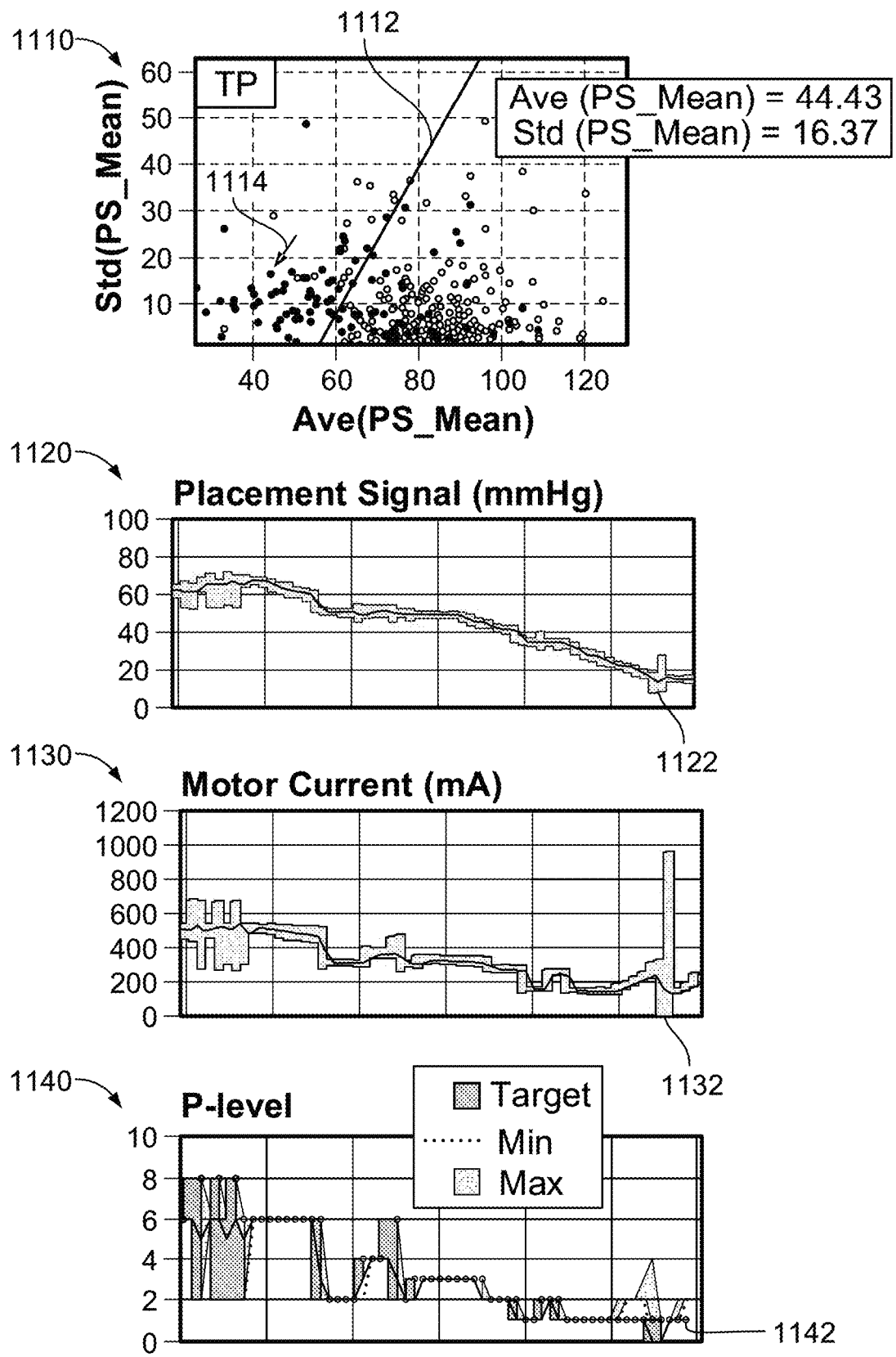
FIG. 11 shows an example of features of a specific patient, Patient Y.

FIG. 11 shows another example of a specific patient, Patient Y. Graph 1110 shows a decision boundary 1112. As described above, an unshaded dot represents survival of a patient, while a shaded dot represents expiration of a patient. Dot 1114 represents Patient Y, who expired. Dot 1114 is located across boundary line 1112 from the majority of the unshaded "survival" dots. The x-axis of graph 1110 represents the average of mean PS, while the y-axis represents the standard deviation of mean PS.

Graph 1120 shows placement signal 1122. The y-axis of graph 1120 represents pressure in mmHg. Graph 1130 shows motor current signal 1132. The y-axis of graph 1130 represents motor current in mA. Graph 1140 shows P-level 1142. The y-axis of graph 1140 represents P-level. The x-axes of graphs 1120, 1130, 1140 represent time. Graphs 1120, 1130, 1140 are shown for the same time period, at the same time scale, for the same patient, Patient Y, represented by dot 1122. Placement signal 1122, motor current signal 1132, and P-level 1142 may be indicative of first data related to time-varying parameters of the heart pump system, as described above. Placement signal 1122, motor current signal 1132, and P-level 1142 may be features of a plurality of features used to determine a heart health index for a patient. In some aspects, the heart health index may be a probability of survival of the patient, which may be used to predict a patient outcome. In this case, the patient outcome (represented by dot 1114) is expiration. Graph 1140 shows the variation of target, minimum, and maximum P-level over time. In some implementations, a clinician varies target P-level to increase or decrease operation of the pump to treat the patient. For example, the clinician may increase or decrease target P-level if the patient's probability of survival decreases. As one example, graph 1140 shows the target P-levels the heart pump system was set to to treat the patient.

The differences between FIG. 10 and FIG. 11 show how measured characteristics representative of a patient, such as placement signal, motor current, and P-level may correlate to a patient's survival for expiration. For example, the Patient X (represented in FIG. 10) survived, while Patient Y (represented in FIG. 11) expired. The systems and methods described herein predicted this outcome based on the standard deviation of PS_mean and the average PS_mean (new log data 108 of FIG. 1) combined with the boundary lines 1412, 1112 (machine learning model 106 of FIG. 1) which were calculated via training data (log data 102 and patient outcome 104 of FIG. 1).

Figure 12:
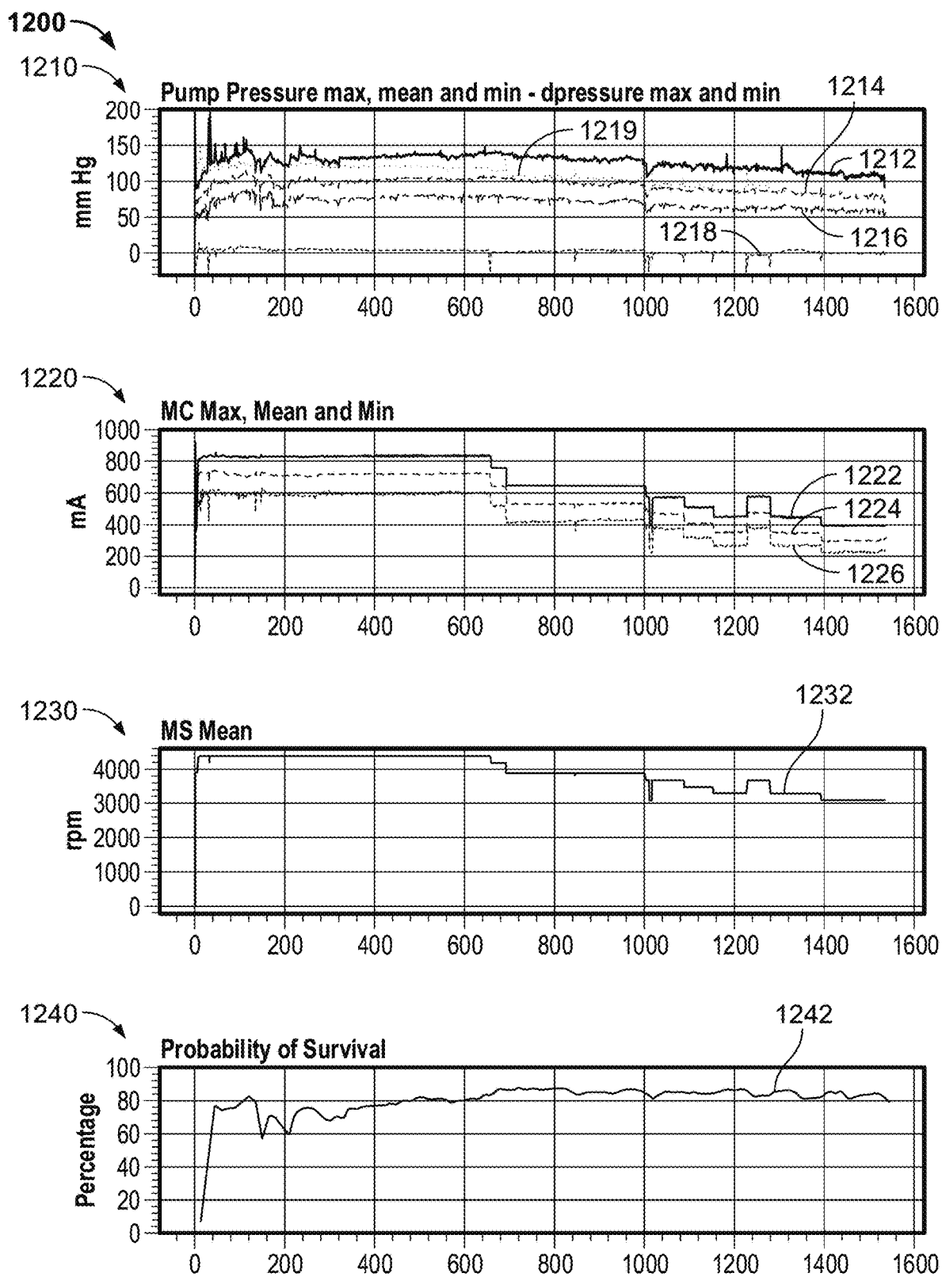
FIG. 12 shows characteristics relating to a patient over time through a set of four graphs.

FIG. 12 shows characteristics relating to a patient over time through a set 1200 of four graphs. Three graphs 1210, 1220, 1230 show measured characteristics relating to the patient over the same time frame. Graph 1210 shows pump pressure maximum 1212, pump pressure mean 1214, pump pressure minimum 1216, differential pressure maximum 1219, and differential pressure minimum 1218. The y-axis of graph 1210 represents millimeters of mercury (mmHg) while the x-axis represents time. Graph 1220 shows motor current maximum 1222, mean 1224, and minimum 1226 for a heart pump system placed in the patient. The y-axis of graph 1220 represents milliAmps (mA), while the x-axis represents time at the same scale and over the same time period as the x-axis of graph 1210. Graph 1230 shows motor speed (MS) mean 1232. The y-axis of graph 1230 represents rotations per minute (rpm), while the x-axis represents time at the same scale and over the same time period as the x-axes of graphs 1210 and 1220. Graph 1240 shows a calculated measure of the patient's heart health, represented as probability of survival 1242. The y-axis of graph 1230 represents the percentage probability of survival of the patient (defined as health status), while the x-axis represents the same time period as described above in relation to graphs 1210, 1220, 1230.

Pump pressure, differential pressure, motor current, and motor speed may be indicative of first data related to time-varying parameters of the heart pump system, as described above. Pump pressure maximum 1212, pump pressure mean 1214, pump pressure minimum 1216, differential pressure maximum 1219, differential pressure minimum 1218, motor current maximum 1222, motor current mean 1224, motor current minimum 1226, and motor speed mean 1232 may be features of a plurality of features used to determine a heart health index for a patient. In some aspects, the heart health index may be the probability of survival 1242 of the patient, which may be used to predict a patient outcome. The patient outcome prediction may change over time.

Probability of survival 1242 may be calculated via the methods and systems described above. The values shown in graphs 1210, 1220, 1230 may be obtained from a heart pump system. Instead of using only the last hour to predict the survival probability (H-index), the probability of survival may be calculated on sliding windows from the start to the end of the case of the patient. Such a process allows the system to monitor the health status of the patient. Probability of survival 1242 is determined at least in part, in this instance, by the pump pressure, motor current, and motor speed. For example, pump pressure, motor current, and motor speed all dip in value just after time marker 1000. There is a corresponding dip in probability of survival 1242 at the same time. Such a dip may be indicative of a decline in heart health of the patient. By predicting a decline in heart health, the system may alert a clinician to a patient health problem before it may be ordinarily determined by the clinician, thereby providing the clinician with more time to treat the patient.

Results of the predictive modeling system are shown in Table 1. The model was tested on 13 shock cases. The shock case data is, in this instance, provided by Henry Ford Hospital as a "third-party" test dataset. Data for the 13 cases is shown in Table 2.

TABLE 2

| Case # | Real Outcome | Predicted Outcome | Survival Probability | Comments |
|---|---|---|---|---|
| 1 | Expired | Expired | 0.05 | Expired in procedure |
| 2 | Expired | Survived | 1 | Survived procedure but expired later |
| 3 | Survived | Expired | 0.41 | Survived, mean pressure is low |
| 4 | Survived | Survived | 0.96 | |
| 5 | Survived | Survived | 0.9 | |
| 6 | Survived | Survived | 0.86 | |
| 7 | Survived | Survived | 0.83 | |
| 8 | Survived | Survived | 0.87 | |
| 9 | Survived | Survived | 0.86 | |
| 10 | Survived | Survived | 0.62 | |
| 11 | Survived | Survived | 0.84 | |
| 12 | Survived | Survived | 0.59 | |
| 13 | Survived | Expired | 0.42 | Ecmo case, we thought patient did not make if from looking at logs |

Another independent test data set (a subset of the data held in the database system described above) was tested. This testing resulted in an accuracy of 81.4%, with N (the number of patients' data used for testing) equal to 80, as shown in Table 3.

TABLE 3

| N = 80 | Random | Model |
|---|---|---|
| Accuracy | 55.8% | 81.4% |
| Precision | 33.0% | 79.1% |
| Sensitivity | 33.0% | 59.8% |

Figure 13:
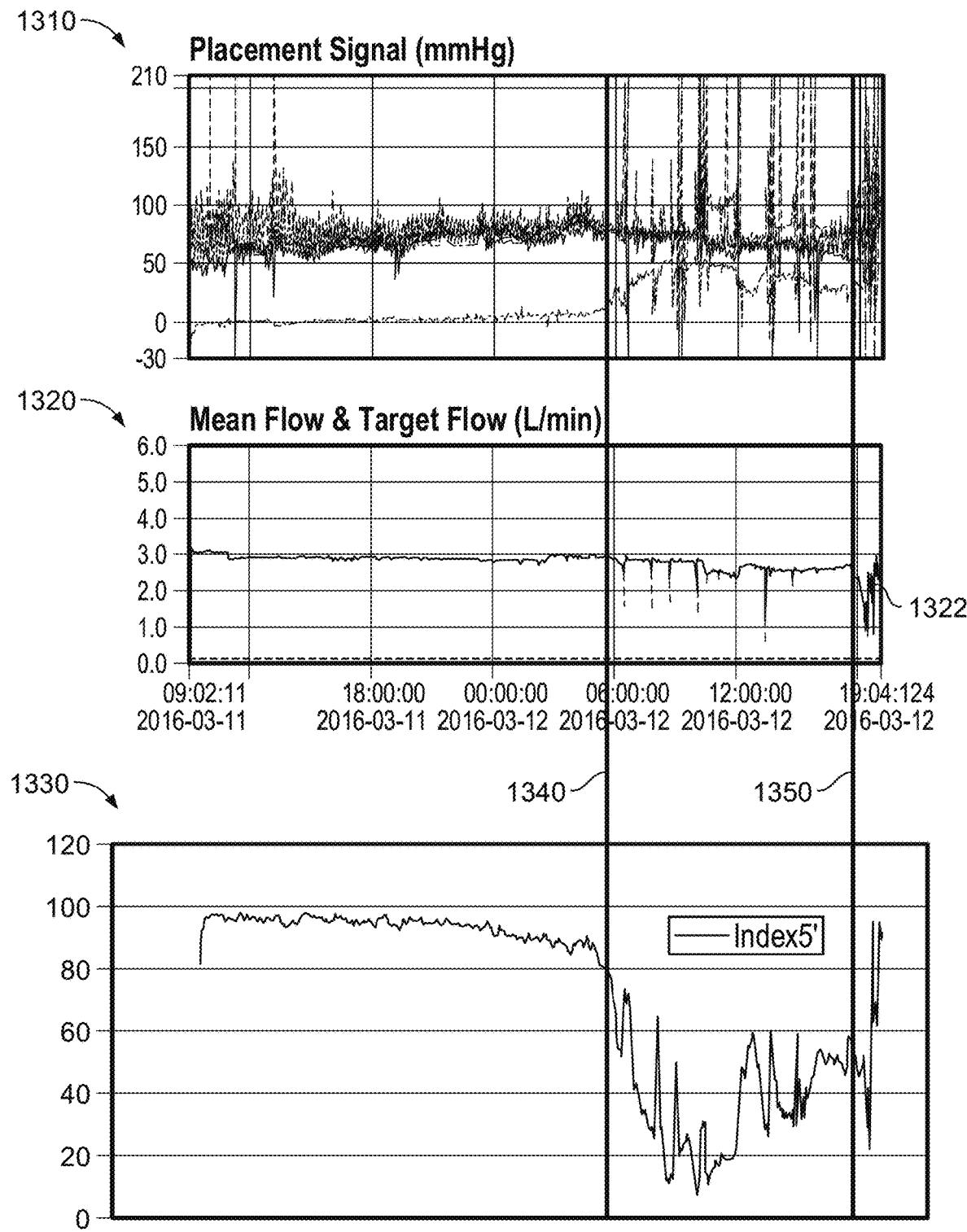
FIG. 13 shows an example of features of a specific patient, Patient Z.

FIG. 13 show features over time for an example case through a set of graphs 2000. Three graphs 1310, 1320, 1330 show characteristics relating to a patient over time. Placement signal graph 1310 has a y-axis showing pressure in millimeters of mercury (mmHg) and an x-axis showing time. Flow graph 1320 has a y-axis showing flow in liters per minute (L/min) and an x-axis showing time. Health index graph 1330 has a y-axis showing heart health index and an x-axis showing time. The time scales of graphs 1310, 1320, 1330 are the same, and graphs 1310, 1320, 1330 are placed such that the x-axes of the three graphs are aligned.

Placement signal and flow may be indicative of first data related to time-varying parameters of the heart pump system, as described above. Placement signal (shown in graph 1310), mean flow and target flow (shown in graph 1320) may be features of a plurality of features used to determine a heart health index for a patient. The index shown in graph 1330 may be the percentage probability of survival of the patient, which may be used to predict a patient outcome. The patient outcome prediction may change over time.

In the example shown in FIG. 13, a patient Z was found unresponsive at home. Patient Z's spouse administered cardiopulmonary resuscitation until emergency services arrived. A heart pump system was placed in Patient Z for 34 hours of support. The x-axis of graphs 1310, 1320, 1330 start approximately at the time of placement of the heart pump system. The mean flow 1322 of the heart system was approximately 3 L/min at P-7 with good performance.

Marker 1340 represents a first point in time, specifically Mar. 12, 2016 at 5:30 am. At marker 2040 Patient Z was hemodynamically stable. Marker 1350 represents a second point in time, specifically Mar. 12, 2016 at 5:45 pm. At marker 1350, Patient Z turned blue. Patient's Z's oxygen saturation (O2 sats) dropped, and Patient Z went into ventricular tachycardia or ventricular fibrillation (VT/VF). Doctors were unable to resuscitate Patient Z.

The time between markers 1340 and 1350 shows significant disruptions to the mean flow 1322 of the heart system and placement signal 1312. As can be seen in graph 1330, the significant disruptions to placement signal 1312 and mean flow 1322 results in a dramatic change in Patient Z's heart health index 1332 between markers 1340 and 1350. A clinician could view the heart health index and determine the patient is at risk. Prior to marker 1340, graphs 1310 and 1320 are relatively steady (when compared to the high variation shown between markers 1340 and 1350). Graph 1330, however, shows a gradual but steady decline in patient health prior to marker 1340. A clinician could view the decline of the heart health index and determine the patient's health is deteriorating. By viewing the decline of the heart health index, a clinician could have intervened before the time represented by marker 1340 (i.e., before the patient's flow and placement signal showed significant disruption). In some cases, early intervention is highly beneficial to patient health and is a determining factor in patient survival. In some examples, if the heart health index is declining (e.g., as shown in graph 1330 prior to marker 1340), a clinician may be alerted to the patient's decline in health so that the clinician may intervene in patient care. The heart health index graph 1330 may also be used in post-case analysis after a patient has expired.

Figure 14:
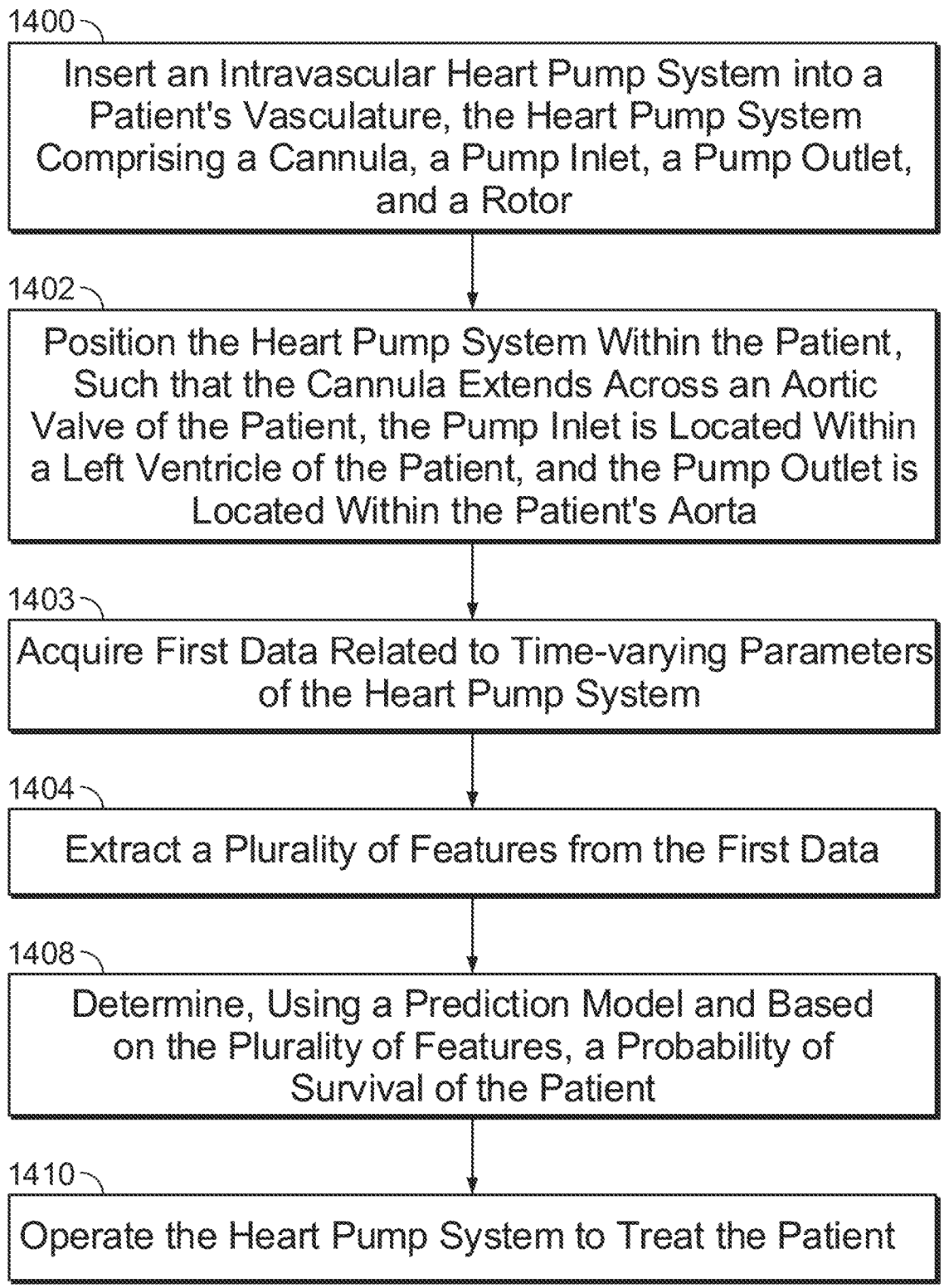
FIG. 14 shows a flowchart of determining a probability of survival of a patient.

FIG. 14 shows a flowchart of determining a probability of survival of a patient. At step 1400, an intravascular heart pump system is inserted into vasculature of the patient. The heart pump system includes a cannula, a pump inlet, a pump outlet and a rotor. In some implementations, the heart pump system is a left ventricular assist device (LVAD). In some implementations, the heart pump system is a right ventricular assist device (RVAD). In some implementations, the cannula, pump inlet, pump outlet, and rotor are optional. At step 1402, the heart pump system is positioned within the patient such that the cannula extends across an aortic valve of the patient, the pump inlet is located within a left ventricle of the patient, and the pump outlet is located within an aorta of the patient. In some implementations, step 1402 is optional and the heart pump system is simply positioned partially within the patient. For example, the heart pump system may be inserted via a catheterization through the femoral artery, into the ascending aorta, across the aortic valve and into the left ventricle or through the femoral vein and into the right atrium.

At step 1403, first data is acquired. The first data relates to time-varying parameters of the heart pump system. The first data may represent continuous or near-continuous measurements acquired via the heart pump system, or represent known quantities such as inputs to the heart pump system. The first data relates to operation of or factors measured by the heart pump system, i.e., without the heart pump system the first data would not be known. The first data may include data indicative of heart rate, pump pressure, differential pressure, motor current, P-level, and/or motor speed. From these measurements, important information about heart function, and in some cases information about the cardiac assist device performance, including the occurrence of suction events, can be determined. This information about heart function can be used to predict a probability of patient survival, as described below in relation to step 1408.

In some implementations, one or sensors on the heart pump system acquire the first data. In some implementations, the first data is acquired through external systems. In some implementations, one or sensors on the heart pump system acquire the first data. The one or more sensors on the heart pump system may be positioned within the patient's heart, outside the patient's heart, or a combination of both, during operation of the heart pump system. For example, sensors on the heart pump system may measure pressure within the patient's vasculature. The measured pressure may be used in the calculation of additional parameters, such as cardiac power output, as described above.

At step 1404, a plurality of features are extracted from the first data. Extracting the features may include processing the first data at the heart pump system or at an external device. The plurality of features may include left ventricular end diastolic pressure (LVEDP), stroke volume, ejection fraction, chamber distention, chamber hypertrophy, chamber pressure, stroke work, preload state, afterload state, heart rate, heart recovery, aortic pressure, differential pressure, motor current, motor speed, pump pressure, left ventricular pressure, end of diastolic pressure, aortic pulse pressure, native cardiac output, cardiac output, CPO, placement, mean flow, target flow, P-level, contractility, relaxation, a placement signal, average placement, standard deviation of placement, average placement range, standard deviation of placement range, average differential pressure, standard deviation of differential pressure, average differential pressure range, standard deviation of differential pressure range, left ventricular pressure maximum, left ventricular pressure minimum, pump pressure maximum, pump pressure mean, pump pressure minimum, differential pressure maximum, differential pressure minimum, motor current maximum, motor current minimum, motor current mean, motor speed mean, any other suitable feature, and any combination thereof.

In some implementations, the first data are acquired during a first time period during which the heart pump system is in operation, such as a second, a minute, five minutes, ten minutes, an hour, a few hours, a day, a few days, a week, a month, or any suitable time frame. The average, mean, and minimum values of the features described above may be the average, mean, or minimum value of a feature during the first time period.

At step 1408, a probability of survival of the patient is determined. Probability of survival is a value that is indicative of a likelihood of patient survival or expiration. In some implementations, the probability of survival is a numerical value, e.g., between 0 and 1. In some implementations, if the probability is greater than or equal to a threshold (e.g., 0.5) the probability of survival indicates survival (e.g., the patient has a greater than 50% chance of living given his or her heart health). The probability of survival is based on the plurality of features extracted in step 1404, described above, and is determined using a prediction model. In some implementations, the prediction model is a machine-learning model. For example, the prediction model may be one of a logistic regression technique, a deep learning technique, a decision tree, a random forest technique, a naïve Bayes technique, a support vector machines technique, or any other suitable model.

At step 1410, the heart pump system is operated to treat the patient. In some implementations step 1410 is optional. In some implementations, the heart pump system may operate to provide a constant or near constant level of support to the patient. In some implementations, the pump operation is altered based on the prediction value of patient outcome. In particular, altering the pump operation may include adjusting the operating parameters of the heart pump system to provide a level of support different than that provided during the time period in which the first data was acquired. In one example, adjusting the operating parameters of the heart pump system includes adjusting pump speed (such as by increasing or decreasing, for example) based on a change in cardiac power output, lactate concentration, or both. It may be desirable to increase pump speed when one feature value is below a first threshold, and when a second feature value is above a second threshold, or both, as described below in relation to FIG. 15.

Figure 15:
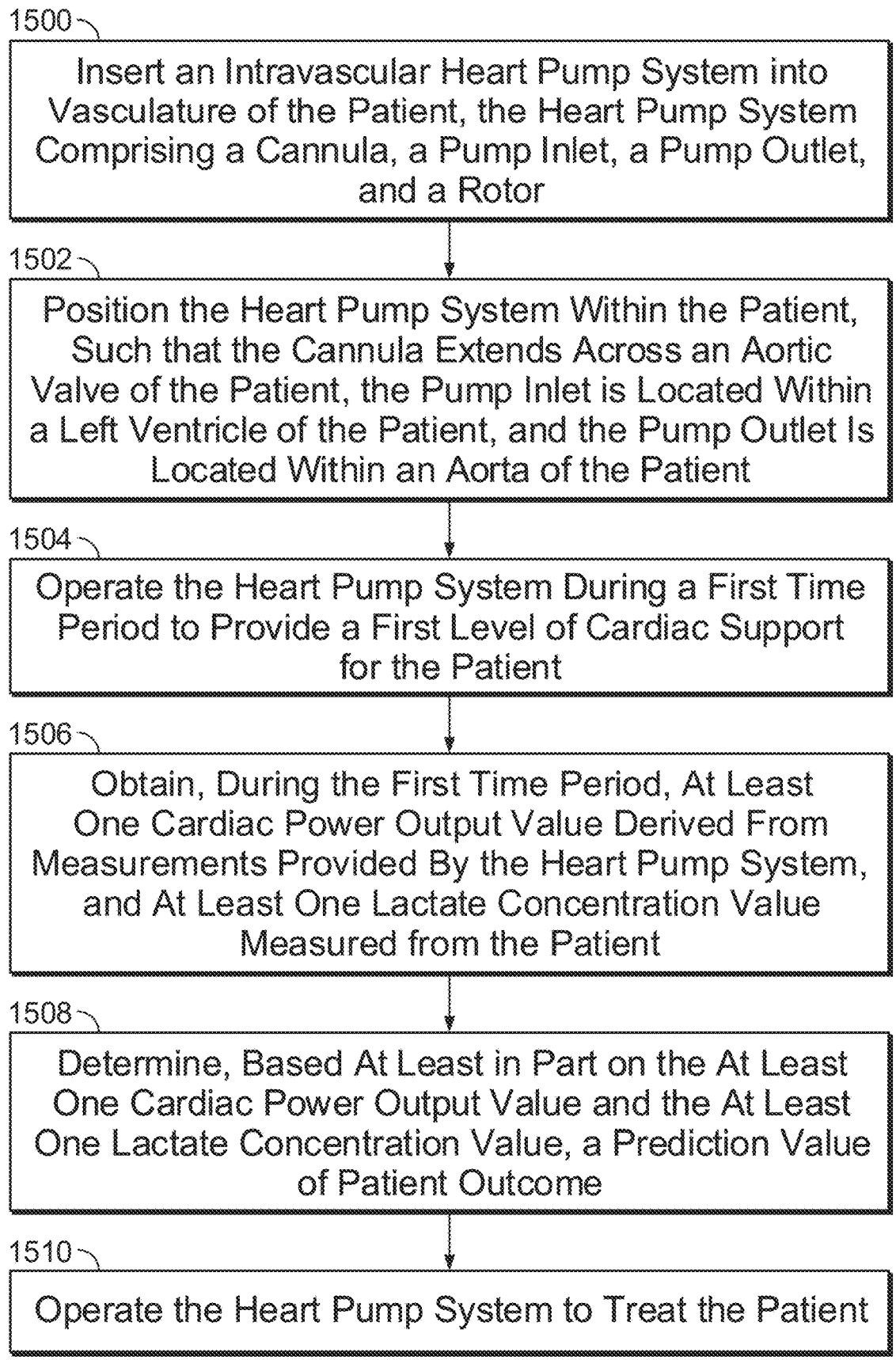
FIG. 15 shows a flowchart of determining a prediction value of patient outcome based on CPO and lactate concentration.

FIG. 15 shows a flowchart of determining a prediction value of patient outcome based on CPO and lactate concentration. Steps 1500 and 1502 are the same as steps 1400 and 1402 described above. At step 1504, the heart pump system is operated during a first time period to provide a first level of cardiac support for the patient. Examples of providing a level of cardiac support include operating the pump at a P-level or motor speed, providing current to the pump motor, turning the pump on, inducing flow through the pump or the patient's heart, or any other suitable method of support. The level at which to operate the heart pump system may be provided by a controller, for example through a user instruction entered via a user interface.

At step 1506, at least one CPO value is obtained. The at least one CPO value is derived from measurements provided by the heart pump system. Optionally, the at least one CPO value is representative of CPO at at least one time point within the first time period described above in relation to step 1504. In some implementations, CPO is updated regularly at fixed time intervals following the first time period. For example, the first time interval may be 0.01 second, 0.1 second, 0.5 second, 1 second, 5 seconds 10 seconds, 1 minute, 10 minutes, 15 minutes, 30 minutes, 1 hour, or any suitable time interval. At step 1506, at least one lactate concentration value is also obtained. The at least one lactate concentration value may be measured from the patient. For example, the lactate concentration value may be manually input into the heart pump system or may be retrieved from an external database.

At step 1508, a prediction value of patient outcome is determined. The prediction value is based at least in part on the at least one cardiac power output value and the at least one lactate concentration value acquired in step 1506. It may be desirable to increase pump speed when the at least one CPO value is below a first threshold, when the at least one lactate concentration value is above a second threshold, or both. For example, the first threshold may be a value such as 0.3, 0.4, 0.5, 0.6, 0.7, 0.8, 0.9, 1.0 W and the second threshold may be a value such as 1, 2, 3, 4, 5, 6, 7 mmol/L. A low CPO value and a high lactate value may indicate the patient has a relatively low probability of survival. Because the patient is not doing well, the clinician may attempt to increase the level of cardiac support provided by the pump, by increasing the pump speed, for example. It may also be desirable to decrease or not change pump speed when the at least one CPO value is above the first threshold, when the at least one lactate concentration value is below the second threshold, or both. A high CPO value and a low lactate value may indicate the patient has a relatively high probability of survival. Because the patient is doing well, the clinician may decide to not change the parameters of the pump's operation. Alternatively, the clinician may attempt to reduce the level of cardiac support provided by the pump, or turn off the pump completely. Step 1510 is the same as step 1410 described above in relation to FIG. 14.

The foregoing is merely illustrative of the principles of the disclosure, and the apparatuses can be practiced by other than the described embodiments, which are presented for purposes of illustration and not of limitation. It is to be understood that the apparatuses disclosed herein, while shown for use in percutaneous insertion of heart pumps, may be applied to apparatuses in other applications requiring hemostasis.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

The systems and methods described may be implemented locally on a heart pump system or a controller of a heart pump system, such as the AIC. The heart pump system may include a data processing apparatus. The systems and methods described herein may be implemented remotely on a separate data processing apparatus. The separate data processing apparatus may be connected directly or indirectly to the heart pump system through cloud applications. The heart pump system may communicate with the separate data processing apparatus in real-time (or near real-time).

In general, embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program may correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A method for treating a patient in cardiogenic shock, the method comprising:
   inserting an intravascular heart pump system into vasculature of the patient, the heart pump system comprising a cannula, a pump inlet, a pump outlet, and a rotor;
   positioning the heart pump system within the patient, such that the cannula extends across an aortic valve of the patient, the pump inlet is located within a left ventricle of the patient, and the pump outlet is located within an aorta of the patient;
   acquiring, from the heart pump system, first data related to time-varying parameters of the heart pump system;
   extracting a plurality of features from the first data;
   determining, using a prediction model and based on the plurality of features, a prediction value of patient outcome; and
   operating the heart pump system based on the determined prediction value of patient outcome.

2. The method of claim 1, wherein the prediction value of patient outcome comprises a cardiac component representative of the patient's heart performance and a system perfusion component representative of the patient's circulatory performance.

3. The method of claim 1 further comprising:
   acquiring second data related to physiological parameters of the patient; and
   wherein determining the prediction value of patient outcome is also based on the second data.

4. The method of claim 3, wherein the second data includes at least one of: age, gender, body surface area (BSA), urine output, creatinine level, potential of Hydrogen (pH), oxygen concentration, carbon dioxide concentration, and lactate concentration.

5. The method of claim 4, wherein the first plurality of features includes cardiac power output and the second data includes lactate concentration.

6. The method of claim 1, wherein a pump operating parameter value is selected based on the prediction value of patient outcome.

7. The method of claim 6, wherein the pump operating parameter is pump speed.

8. The method of claim 7, wherein the pump speed is increased based on the prediction value of patient outcome.

9. The method of claim 1 further comprising:
   acquiring a plurality of prediction values of patient outcome including the prediction value of patient outcome, each prediction value of patient outcome corresponding to a time period of a plurality of time periods; and
   determining, based on the plurality of prediction values of patient outcome, a change in patient health.

10. The method of claim 1, wherein the plurality of features includes at least one of: aortic pressure, differential pressure, motor current, motor speed, pump pressure, left ventricular pressure, end of diastolic pressure, aortic pulse pressure, native cardiac output, cardiac output, cardiac power output, placement, mean flow, target flow, P-level, contractility, relaxation, a placement signal, average placement, standard deviation of placement, average placement range, standard deviation of placement range, average differential pressure, standard deviation of differential pressure, average differential pressure range, standard deviation of differential pressure range, left ventricular pressure maximum, left ventricular pressure minimum, pump pressure maximum, pump pressure mean, pump pressure minimum, differential pressure maximum, differential pressure minimum, motor current maximum, motor current minimum, motor current mean, and motor speed mean.

11. The method of claim 1, wherein the prediction model is a machine-learning model that is one of: a logistic regression technique, a deep learning technique, a decision tree, a random forest technique, a naïve Bayes technique, and a support vector machines technique.

12. The method of claim 1 further comprising:
   displaying an indicator of a relative importance of a first feature of the plurality of features compared to a second feature of the plurality of features.

13. The method of claim 1, wherein determining the prediction value of patient outcome comprises:
   acquiring, from a database, a training dataset comprising a plurality of data points relating to time-varying parameters of a heart pump system;
   pre-processing the dataset to determine a third plurality of features corresponding to the plurality of data points;
   processing the third plurality of features to determine a pattern, wherein the pattern comprises a weight of each feature of a subset of the third plurality of features;
   acquiring patient data; and
   calculating, based on the patient data and the pattern, the prediction value of patient outcome.

14. The method of claim 1, wherein the prediction value of patient outcome indicates expiration or survival of the patient.

15. A heart pump system comprising:
   a pump comprising a pump housing, a rotor, and an opening positioned proximal of the pump housing;

a cannula comprising a proximal end that interfaces with a distal end of the pump housing and a distal end with at least one distal opening, the pump being configured to be operated by a motor;

an elongate catheter extending proximal of the pump housing;

at least one sensor configured to acquire first data related to time-varying parameters; and a controller configured to:

determine, based on the first data, a prediction value of patient outcome; and operate the pump based on the determined prediction value of patient outcome.

16. The heart pump system of claim 15, further comprising a flexible projection extending distally away from the distal end of the cannula.

17. The heart pump system of claim 15, further comprising an integrated motor sized and configured for insertion into a patient's vasculature.

18. The heart pump system of claim 17, wherein the motor is configured to maintain a substantially constant rotor speed during actuation of the rotor.

19. The heart pump system of claim 15, wherein the elongate catheter is coupled on its distal end to the pump housing, and wherein the pump further comprises a drive cable extending through the elongate catheter.

20. The heart pump system of claim 15, wherein the pump is configured to be placed such that cannula extends across an aortic valve of a patient, the distal end being located within a left ventricle of the patient, and the proximal end being located within an aorta of the patient.

* * * * *